US006974450B2

(12) United States Patent
Weber et al.

(10) Patent No.: US 6,974,450 B2
(45) Date of Patent: Dec. 13, 2005

(54) FACE-LIFTING DEVICE

(75) Inventors: Paul J. Weber, Ft. Lauderdale, FL (US); Luiz B. Da Silva, Danville, CA (US); Alexander M. Rubenchik, Livermore, CA (US)

(73) Assignee: Pearl Technology Holdings, LLC, Livermore, CA (US)

( * ) Notice: Subject to any disclaimer, the term of this patent is extended or adjusted under 35 U.S.C. 154(b) by 0 days.

(21) Appl. No.: 09/749,497

(22) Filed: Dec. 22, 2000

(65) Prior Publication Data

US 2001/0025190 A1 Sep. 27, 2001

Related U.S. Application Data

(63) Continuation-in-part of application No. 09/475,635, filed on Dec. 30, 1999, now Pat. No. 6,440,121, and a continuation-in-part of application No. 09/478,172, filed on Jan. 5, 2000, now Pat. No. 6,432,101, and a continuation-in-part of application No. 09/588,436, filed on Jun. 6, 2000, now Pat. No. 6,391,023.

(51) Int. Cl.[7] ............................................. A61B 18/18
(52) U.S. Cl. .................. 606/2; 606/9; 606/15; 128/898
(58) Field of Search ...................... 606/2–3, 7, 10–17, 606/32, 41, 50, 45, 9

(56) References Cited

U.S. PATENT DOCUMENTS

| | | | | |
|---|---|---|---|---|
| 4,582,057 A | * | 4/1986 | Auth et al. .................. 219/229 |
| 5,647,867 A | * | 7/1997 | Neuberger et al. ............ 606/15 |
| 5,693,043 A | * | 12/1997 | Kittrell et al. ................. 606/15 |
| 5,695,510 A | | 12/1997 | Hood .......................... 606/169 |
| 5,755,753 A | | 5/1998 | Knowlton .................... 607/98 |
| 5,776,092 A | | 7/1998 | Farin et al. .................... 604/22 |
| 5,827,267 A | * | 10/1998 | Savage et al. ................ 606/14 |
| 5,871,524 A | | 2/1999 | Knowlton .................... 607/101 |
| 5,873,855 A | | 2/1999 | Eggers ......................... 604/114 |
| 5,919,219 A | | 7/1999 | Knowlton .................... 607/102 |
| 5,935,143 A | | 8/1999 | Hood .......................... 606/169 |
| 5,948,011 A | | 9/1999 | Knowlton .................... 607/101 |
| 5,984,915 A | | 11/1999 | Loeb et al. .................... 606/9 |
| 6,033,398 A | * | 3/2000 | Farley et al. ............... 604/113 |
| 6,135,999 A | * | 10/2000 | Fanton et al. ................. 606/45 |
| 6,176,854 B1 | | 1/2001 | Cone .......................... 606/15 |
| 6,241,753 B1 | | 6/2001 | Knowlton .................... 607/99 |
| 6,264,652 B1 | | 7/2001 | Eggers et al. ................. 606/41 |
| 6,277,116 B1 | | 8/2001 | Utely et al. ................... 606/42 |
| 6,311,090 B1 | | 10/2001 | Knowlton .................... 607/101 |
| 6,346,105 B1 | * | 2/2002 | Tu et al. ....................... 606/41 |

(Continued)

OTHER PUBLICATIONS

"Ideas and innovations: the Bulbous-Lysing Underminer". Weber et al. (Journal of Dermatologic Surgery and Oncology) 15: 1252-1253,1989.
P.J. Weber et al., Bulbous-Lysing Underminers, J. Dermatol Surg. Oncol., 15:12, Dec. 1989, pp. 1252-1253.

*Primary Examiner*—John P. Leubecker
*Assistant Examiner*—Pete Vrettakos
(74) *Attorney, Agent, or Firm*—John P. Wooldridge

(57) ABSTRACT

A device is described that can be used by surgeons to provide quick and accurate face-lifting maneuvers that minimize the amount of tissue that has to be removed. The device is comprised of a shaft with a relatively planar but possibly lenticulate and even slightly curved tip that can divide and energize various tissue planes causing contraction especially via the fibrous tissues. Various forms of energy can be delivered down the shaft to heat and cause desirable tissue contraction. The device can also include a temperature sensor that can be used to control power output.

45 Claims, 13 Drawing Sheets

U.S. PATENT DOCUMENTS

| | | | |
|---|---|---|---|
| 6,350,276 B1 | 2/2002 | Knowlton | 607/104 |
| 6,377,854 B1 | 4/2002 | Knowlton | 607/101 |
| 6,377,855 B1 | 4/2002 | Knowlton | 607/101 |
| 6,381,497 B1 | 4/2002 | Knowlton | 607/101 |
| 6,381,498 B1 | 4/2002 | Knowlton | 607/101 |
| 6,387,380 B1 | 5/2002 | Knowlton | 424/400 |
| 6,391,023 B1 * | 5/2002 | Weber et al. | 606/15 |
| 6,405,090 B1 | 6/2002 | Knowlton | 607/102 |
| 6,413,255 B1 | 7/2002 | Stern | 606/41 |
| 6,419,674 B1 * | 7/2002 | Bowser et al. | 606/45 |
| 6,425,912 B1 | 7/2002 | Knowlton | 607/101 |
| 6,430,446 B1 | 8/2002 | Knowlton | 607/101 |
| 6,432,101 B1 * | 8/2002 | Weber et al. | 606/2 |
| 6,438,424 B1 | 8/2002 | Knowlton | 607/101 |
| 6,453,202 B1 | 9/2002 | Knowlton | 607/102 |
| 6,461,350 B1 | 10/2002 | Underwood | 606/32 |
| 6,461,354 B1 | 10/2002 | Olsen | 606/41 |
| 6,461,378 B1 | 10/2002 | Knowlton | 607/104 |
| 6,470,216 B1 | 10/2002 | Knowlton | 607/101 |
| 6,482,201 B1 | 11/2002 | Olsen | 606/41 |
| 6,514,248 B1 | 2/2003 | Eggers | 606/41 |
| 6,544,261 B2 | 4/2003 | Ellsberry | 606/41 |
| 6,557,559 B1 | 5/2003 | Eggers | 128/898 |
| 6,595,990 B1 | 7/2003 | Weinstein | 606/41 |
| 6,623,454 B1 | 9/2003 | Eggers | 604/114 |
| 6,632,193 B1 | 10/2003 | Davison | 604/22 |
| 6,632,220 B1 | 10/2003 | Eggers | 606/41 |
| 6,659,106 B1 | 12/2003 | Hovda | 128/898 |
| 6,719,754 B2 | 4/2004 | Underwood | 606/32 |
| 6,740,079 B1 | 5/2004 | Eggers | 606/34 |
| 2002/0128648 A1 * | 9/2002 | Weber et al. | 606/45 |

* cited by examiner

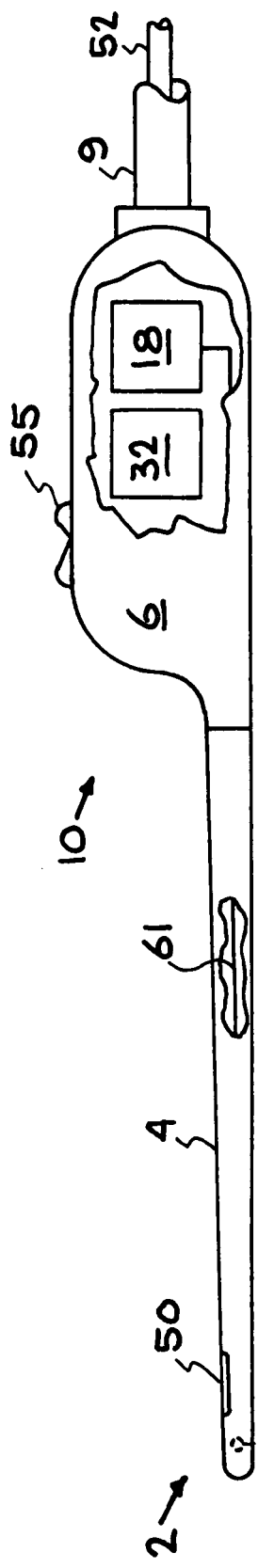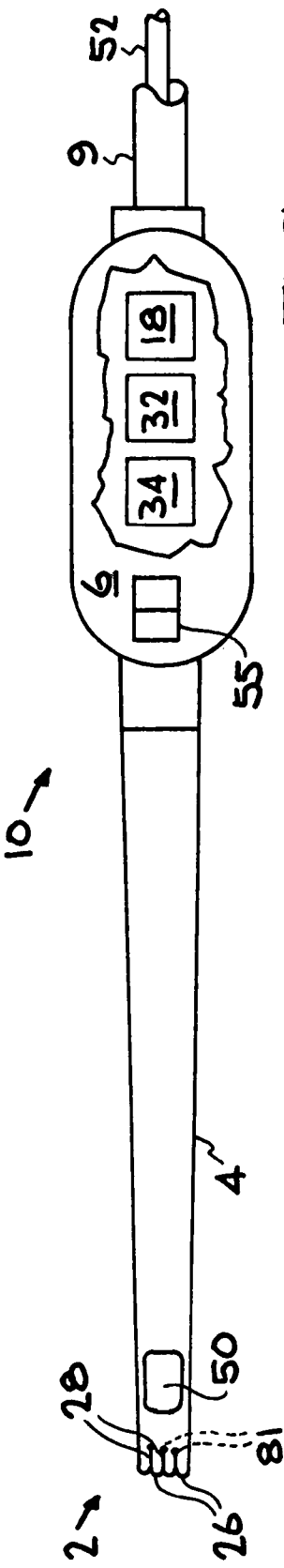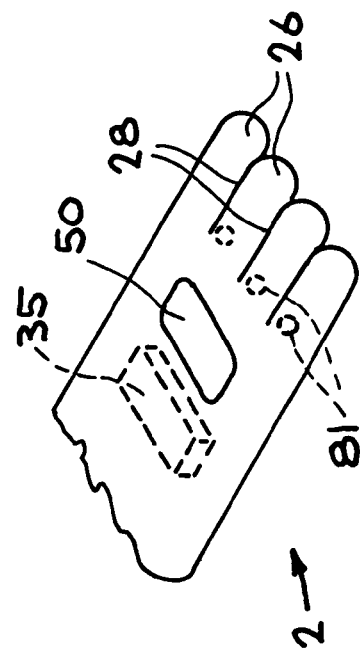

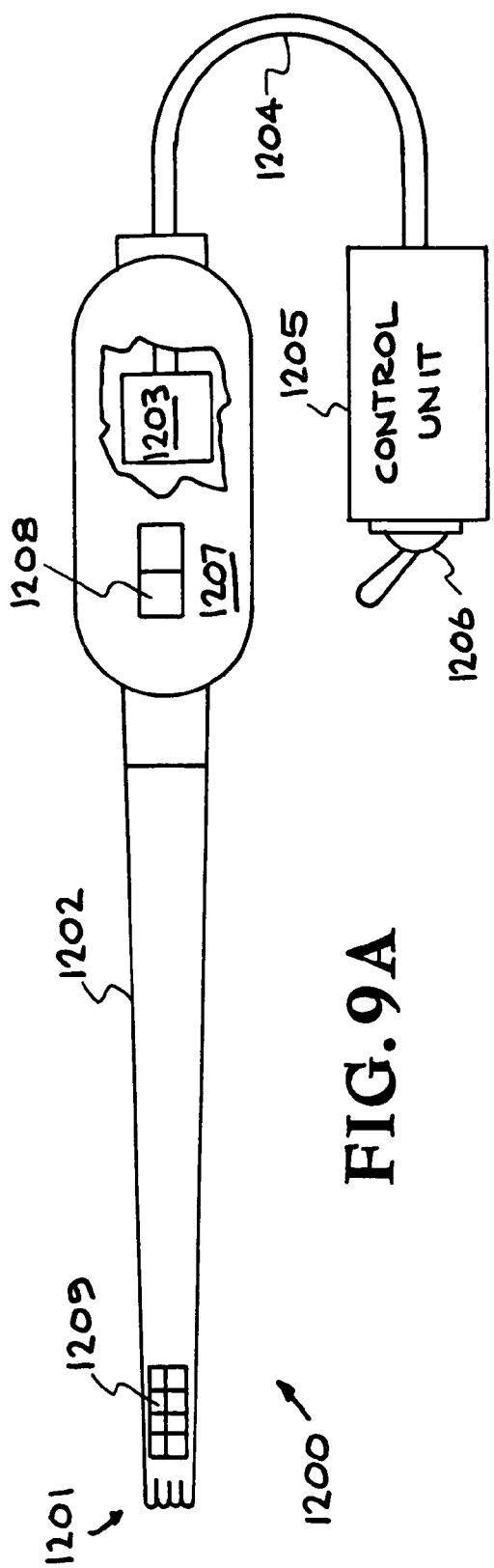
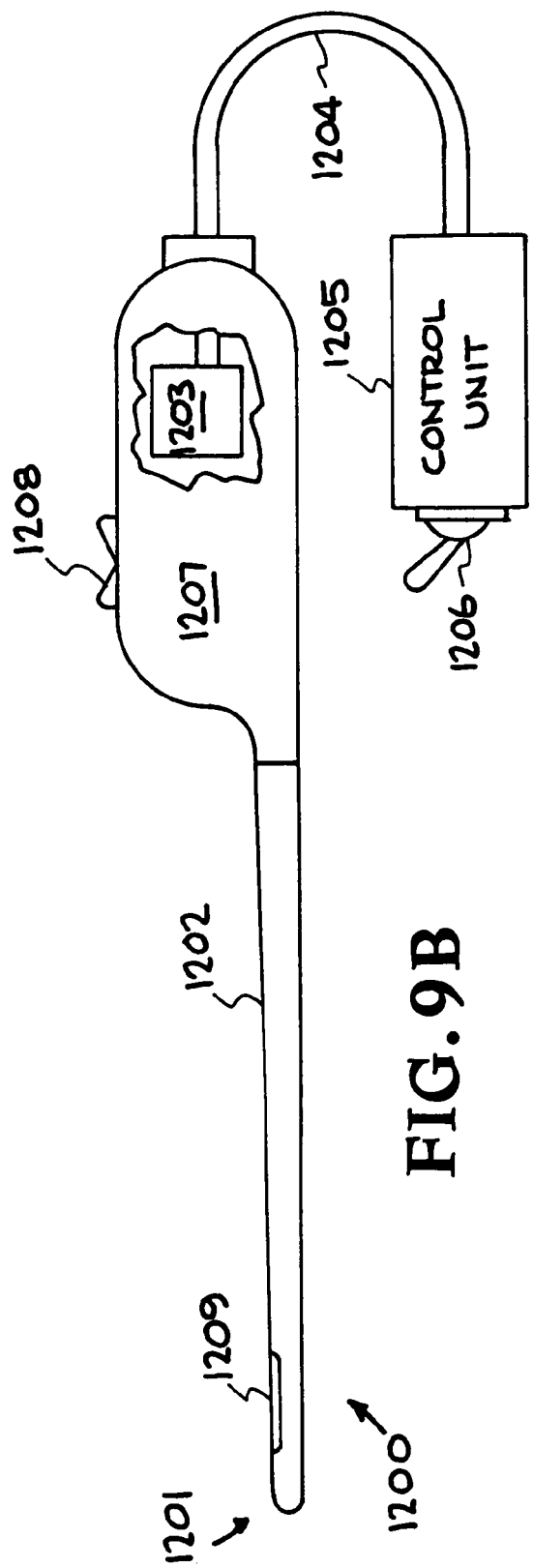
FIG. 9A
FIG. 9B

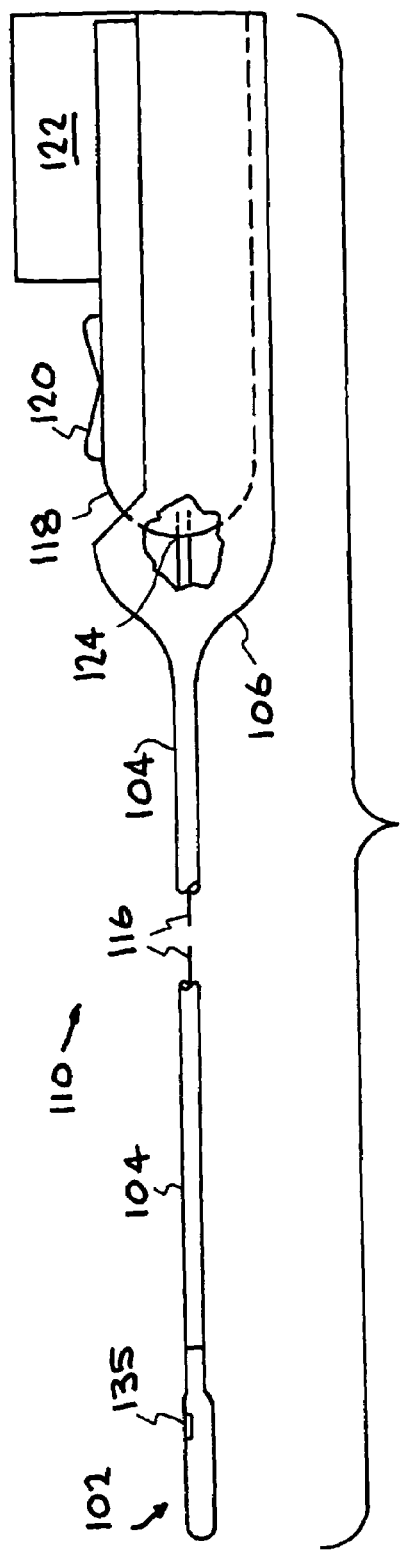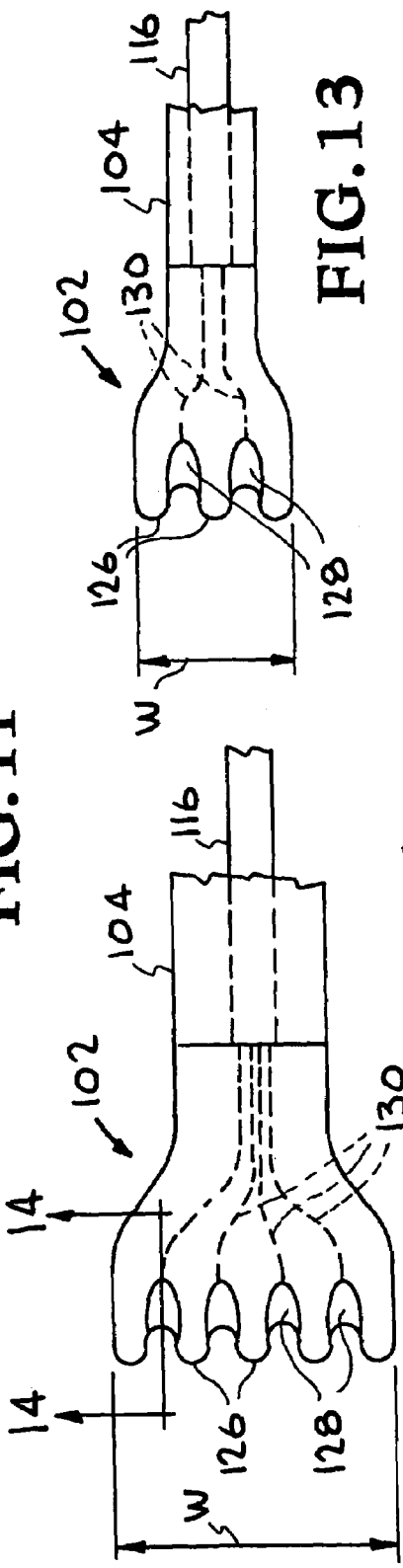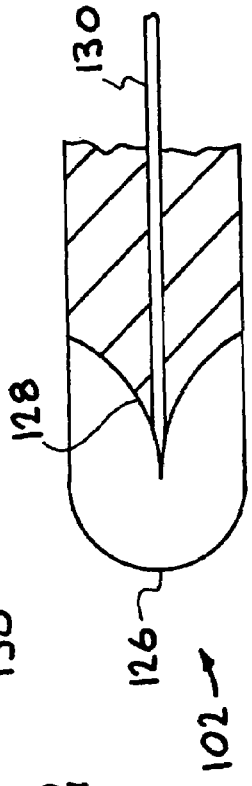

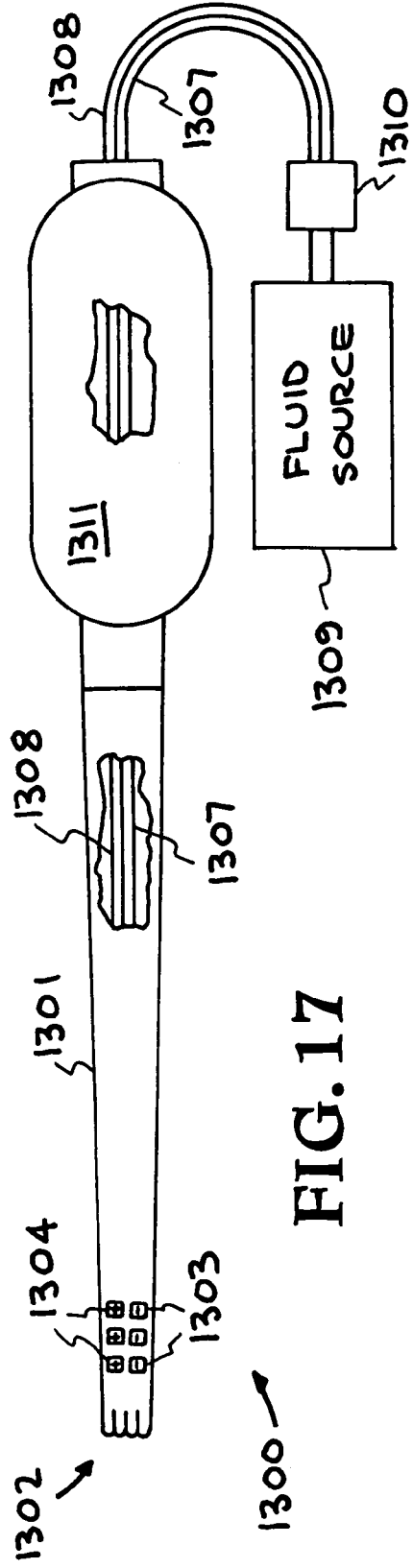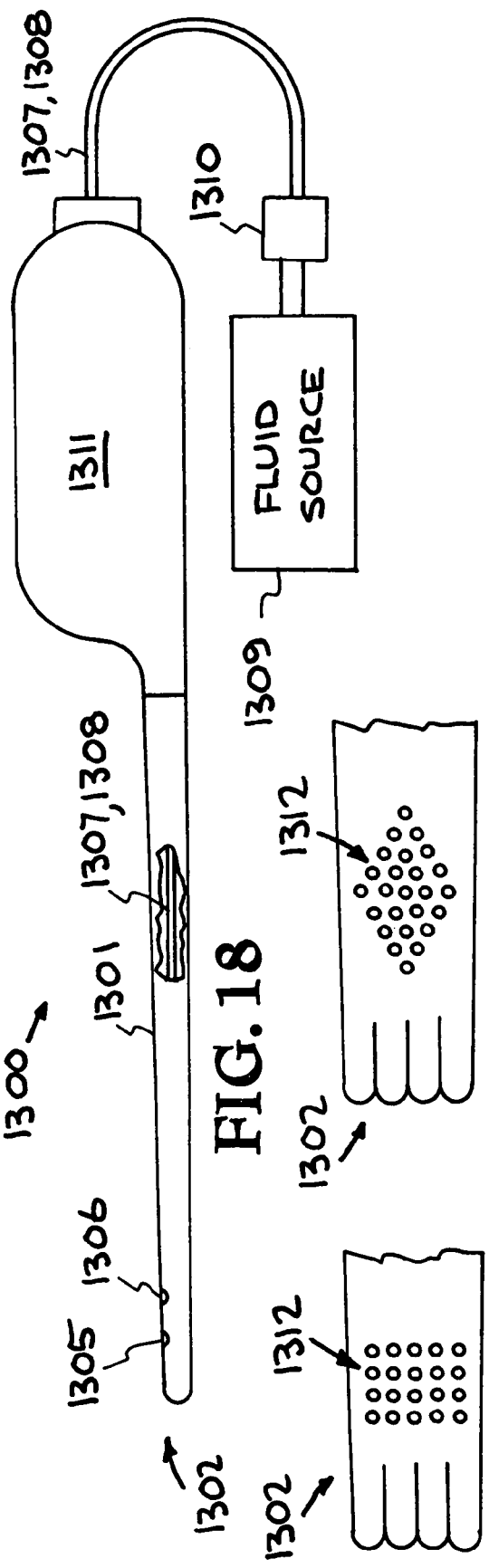
FIG. 17  FIG. 18  FIG. 19A  FIG. 19B

FACE-LIFTING DEVICE

This application is a continuation-in-part of U.S. patent application Ser. No. 09/475,635, now U.S. Pat. No. 6,440,121, titled "Surgical Device For Performing Face-Lifting Surgery Using Radio Frequency Energy", filed Dec. 30, 1999 and U.S. patent application Ser. No. 09/478,172, now U.S. Pat. No. 6,432,101, titled "Surgical Device For Performing Face-lifting Surgery Using Electromagnetic Radiation", filed Jan. 5, 2000 and U.S. patent application Ser. No. 09/588,436, now U.S. Pat. No. 6,391,023, titled "Thermal Radiation Facelift Device", filed Jun. 6, 2000, all incorporated herein by reference.

BACKGROUND OF THE INVENTION

1. Field of the Invention

The invention relates to face-lifting devices, and more specifically, it relates to a surgical device for performing face-lifting while altering the tissue planes on the undersurface of the face using various forms of energy.

2. Description of Related Art

Definitions, Critical Anatomy and Nomenclature:

Cutting (in surgery) will be defined as relatively cleanly breaking through similar or dissimilar tissues with minimal adjacent tissue trauma and thus little tissue stretching, tearing or ripping. Lysis (in surgery) will be defined as breaking through similar or dissimilar tissues with or without adjacent tissue trauma and may involve stretching, tearing or ripping. Depending upon the tissues lysed, the degree of stretching or tearing of lysed tissue edges may be inconsequential or may even result in a desirable benefit such as post surgical contraction. Planes of tissue are not often flat and represent the curviform intersection of dissimilar tissues and are made at least partly of fibrous tissues, either loose and spongy or firm and tough. Planes between the soft internal organs are usually loose and spongy. Planes of tissues in the face and on bones are firm and tough. Undermining will be defined as tissue separation either within or between defined tissue planes. Undermining may be sharp (instrument) or dull (instrument) depending upon the amount of fibrous tissue binding or existing between the tissue planes to be separated. Undermining is usually performed, as is most surgery, with the intention of minimizing trauma. Sharp instrument undermining is usually performed to separate highly fibrous or collagenous tissues; however, sharp undermining suffers from the risk of penetrating adjacent tissues inadvertently because of loss of ability to follow the desired plane. Inability to follow or maintain the plane in sharp undermining is frequently due to limited visibility, difficulty "feeling" the fibrous plane, or scarring (collagen fibrosis) resulting from previous trauma or surgery. Even experienced surgeons may from time to time lose the correct plane of sharp undermining; great skill is required. Blunt undermining allows a rounded, non-sharp tipped, instrument or even human finger to find the path of least resistance between tissues; once the desired plane is found by the surgeon, it is easy to maintain the plane of blunt undermining until the task is complete. Unfortunately, blunt undermining between highly fibrous tissues such as the human face usually causes tunneling with thick fibrous walls. Dissection usually implies sorting out and identification of tissues and usually implies that some sort of undermining has been performed to isolate the desired structure(s). In face-lifting surgery, plastic surgeons have so commonly used the terms undermining and dissection interchangeably that they have become synonymous in this specific situation. Tracking means to maintain a direction of movement upon forcing a tissue-separating instrument without unpredictable horizontal movement or leaving the desired tissue plane(s). Planar tracking means to stay in the same tissue planes. Linear tracking means to move uniformly in a straight or uniformly curved path without unpredictable movement. Groups of linear tracks may form a network that creates an undermined tissue plane.

Anatomical Perspective: Lysis or undermining in one dimension (linear=x) implies forming a tunnel. Lysing or undermining in 2 dimensions at any one instant forms a plane (x,y). Traditional face-lift undermining is done just under the leather (dermis) layer of the skin where dermis joins underlying fat (or subcutaneous (SQ) fat). Even deeper within the SQ fat run larger blood vessels and delicate, non-regenerating motor nerves to the muscles that give the human face motion and expression. Trauma to these nerves can cause a permanent facial deformity or palsy. Deep beneath the SQ fat reside the muscles and glands of the face. (The relevant face-lift anatomy is described in Micheli-Pellegrini V. Surgical Anatomy and Dynamics in Face Lifts. Facial Plastic Surgery. 1992:8:1–10. and Gosain A K et al. Surgical Anatomy of the SMAS: a reinvestigation. Plast Reconstr Surg. 1993: 92:1254–1263. and Jost G, Lamouche G. SMAS in rhytidectomy. Aesthetic Plast Surg 6:69, 1982.) The SQ fat differs from body location to body location. On the face, the SQ fat has many fiber-bundles (septae) carrying nerves and blood vessels. If a surgeon were to move, shove, or forwardly-push a blunt, dull-tipped, 1-inch chisel or pencil shaped device through the fat of the face where SQ abuts the dermis, the sheer thickness of the fiber bundles would likely cause slippage of the device and result in the formation of pockets or tunnels surrounded by compacted fiber bundles or septae. Proper performance of a face-lift involves breaking the septae at a proper level to avoid damaging more important structures such as blood vessels and nerves and glands.

Disadvantages of the current techniques are numerous. Face-lifting devices described in the prior art resemble undermining devices that were constructed with cutting edges that rely entirely on the skill of the surgeon to maintain control. Inadvertent lateral cutting or tissue trauma may be difficult to control. In addition, speed of separation is important to reduce the time that the patient is exposed to anesthetic drugs; time duration of anesthesia may be directly related to the risk of anesthetic complications. There are two principle locations for face lift undermining (dissection). In the more common lower facelift (cheek/neck-lift), undermining in the subcutaneous tissues is customarily performed; in the less common upper facelift (which approximates brow-lifting) undermining in the subgaleal or temporalis fascia plane is customarily performed. Use of prior art undermining devices (including scissors, sharp rhytisectors, etc.) in these planes during cosmetic surgery has, at times, resulted in unwanted cutting, trauma or perforation of adjacent structures. Scissors and rhytisectors are planar cutting instruments; thus, the position of the cutting edges with respect to the surface of the face is controllable only by the surgeon who must estimate cutting edge's location as no $3^{rd}$ dimensional bulbous limitation exists. Unfortunately, scissors with 3 dimensionally "bulbous", rounded tips cannot close all the way to cut target tissue. Scissors with 2 dimensionally rounded tips can close all the way to cut target tissue but may wander inadvertently between tissue planes due to the thin third dimension (thickness) of the scissors blades.

Current face-lifting instruments that cut with other than manual energy do not address the novel concept of a "protected plane" during energized face-lifting dissection. Current lasers must be fired from positions outside the patient to energize tissue within the face to cut in a very imprecise fashion. (See "Manual of Tumescent Liposculpture and Laser Cosmetic Surgery" by Cook, R. C. and Cook, K. K., Lippincott, Williams, and Wilkins, Philadelphia ISBN: 0-7817-1987-9, 1999) Tissue is damaged with little control. Complications from the aforementioned technique have been summarized by Jacobs et al. in Dermatologic Surgery 26: 625–632, 2000.

Current electrosurgical devices for use in general surgery must be delivered through large open pockets or through the limited access and slow moving, tedious endoscopes if they are to see use in face-lifting. None are similar in shape or function to the instant invention.

U.S. Pat. No. 5,776,092 by Farin describes a single tube device that can deliver laser, ultrasound or radio frequency devices to treat tissue. However, Farin's device is not intended for separating tissue planes and is susceptible to catching, tearing or puncturing the tissue when manipulated. It would be advantageous to provide a safe harbor for the precise application of energy to proper face-lift tissues to be separated and energized while excluding vital structures such as nerves and delicate vessels and maintaining an exact distance from the very delicate surface of the skin. It would be additionally advantageous for the same provisions to allow for a uniform forward tracking and feel of motion of the device that provides a surgeon with instantaneous knowledge. Properly sized and placed protrusions and recessions address all of these problems in a manner not previously possible.

One of the most recent competing procedures to incompletely dissect/lyse/cut a face-lift plane is traditional or ultrasonic liposuction. Unfortunately, dissection is incomplete as relatively round cannulas only make round tunnels. The tissues between the tunnels must be cut in a separate step by the surgeon using scissors in order to create a plane. During this separate step, when the scissors cuts the fiber tissues and blood vessels constituting the walls of the tunnels, bleeding and trauma occur and frequently require spot coagulation under visualization. Other severe drawbacks of the incomplete undermining that liposuction cannulas perform is the common trauma and resultant mouth droop paralysis that occurs in the hands of even prominent surgeons when the delicate and anatomically unpredictable (20% of the population) marginal mandibular nerve is cut. Additionally, ultrasonic cannulas become hot and can cause thermal burns called "end hits" when the cannula tip is thrust against the inside of the skin as is common during the procedure.

Just as sharp undermining or dissection has its disadvantages, as previously mentioned, blunt dissection suffers from its own difficulties as well. Forcing a blunt object through tissue avoids indiscriminate sharp cutting of important structures (nerves, vessels). Blunt undermining compacts the stronger, firmer, strands of collagen even contained within tissues as soft fat into thicker "bands" (some overly thick for uniform cutting). Undesirably for a face-lift, traditional blunt object undermining may indiscriminately force aside and compact fibrous tissue septae causing incomplete lysis or freeing of the tissues. Also unfortunately for face-lifting, traditional purely-blunt-object undermining will result in random motion or uncontrollable-slippage of the underminer tip on forward motion and thusly loss of precise tracking of the underminer through target tissue.

Currently it takes surgeons between 20 minutes and one hour to carefully dissect/undermine/lyse/lift a lower face while caring to coagulate blood vessels. It usually takes between 10 minutes and 30 minutes, depending upon the patient to spot coagulate/seal all of the blood vessels that were cut during the aforementioned lysing portion of the face-lifting. For upper face-lifting, times are less than half that mentioned for lower face-lifting. The principle preferred embodiment of the invention would reduce time for a surgeon to do both the duties of lysing and coagulation since the device performs both tasks as well as aids in maintaining proper positioning and tracking. The time reduction should be at least 50–75%. Reduced operating time means less time a wound is open to potential infection, lowered surgical costs and less time and therefore less risk under anesthesia and thus a general improvement in the procedure.

There exists a special subset of the general population that may benefit uniquely from the present invention. Men and women between the ages of 45 and 55 are just beginning to droop and develop folds. However, there is not much undulating wrinkling as in older patients. Currently long incisions of 10–20 cm are made around each of the two ears, for the purposes of hiding the scars; skin is cut out and discarded and the remaining skin stretched. Skin does not thicken in response to stretching; it only thins. Unfortunately, some plastic surgeons in the early 1990's advocated "prophylactic" or "preemptive" face-lifting on women in their 40's purportedly to "stay ahead of nature." This philosophy has now been discounted and discredited by the vast majority of reputable experts.

Given the disadvantages and deficiencies of current face-lifting techniques, a need exists for a device that provides a fast and safe alternative. The present invention combines a unique lysing design with various forms of energy to efficiently lyse and simultaneously induce contraction desirable in face-lifting. The present invention provides a process for human face-lifting, which can be used in hospitals as well as office-based surgery and minimizes pain and risk of injury.

SUMMARY OF THE INVENTION

It is an object of the present invention is to provide a method and a device that can be used by surgeons to provide quick and accurate face-lifting or tightening maneuvers that minimize the amount of tissue that has to be removed.

It is another object of the invention to provide a surgical face-lifting device that easily maintains the proper dissection plane while lysing and delivers energy to the internal collagenous tissues of the face during tangential movement to induce skin tightening. This would be exemplified by the protrusion/recession version of the tip.

Another object of the invention is to provide an undermining device that can position lysing surfaces at a proper level for controlled and safe fibrous tissue separation during a face-lift.

The device is comprised of a hollow or solid shaft with a relatively planar tip that can be easily positioned between dissection planes in tissue and then manipulated to separate tissue planes and lyse fibrous tissue. It has been shown that thermal effects of energy application to the collagenous (dermal, superficial platysma musculature and other) tissues of the face in the facelift plane can cause cosmetically desirable contraction of the dermal tissues with beneficial tightening of the facial tissues. Accordingly, the invention provides an energy source and delivering means, which delivers energy to the distal end of the shaft. A temperature sensor monitors the tissue temperature, and control electronics process temperature information to control the power output for optimum tissue contraction. An optional secondary light source that is visible to the surgeon can be used to help visualize the location of the laser exit window. The various forms of energy that may be used to energize various portions of the device are multi-chromatic light, monochromatic light, laser light, radio frequency electrical energy, vibrational energy, ultrasonic energy, microwave energy, thermal energies or any combination thereof.

An embodiment of the invention has a plurality of protruding members on the distal end of the shaft separated by at least one interstitial lysing segment, wherein the lysing segment is recessed relative to the protruding members.

In another embodiment, the bulbous-lysing (projection-recession) tip is absent. A planar, round or geometric shaft may terminate in some geometry of tip that is nonetheless relatively planar. The tip shape when seen from above or below may be rounded, squared, rectangular, serrated, scalloped, grooved, or geometric. Curved and lenticulate shapes may also be used. The tip shape when seen from the frontal view may be oval, rectangular, serrated, scalloped, grooved, or geometric.

Although an embodiment provides a shaft that has a cross-sectional shape that is flat or planar, acceptable alternative versions of the shaft may be oval, circular, trapezoidal or geometric on cross-section. Although an embodiment provides a tip having a shape with alternating protrusions and recessions, acceptable alternative versions of the tip shape may be semicircular, lenticulate or geometric. Alternatively, a non-energized protrusion-recession shaped tip may be used as well as other traditional instruments such as scissors to create the lift plane; this would be followed some time later, seconds to minutes, by the passage of a (non-tangentially) energized device lacking the preferred tip shape.

In one embodiment of the invention, the user sets the desired tissue temperature on an external control unit using a touch pad or other user interface. The shaft of the device is then inserted through a small (~1 cm long) incision and positioned at the desired tissue plane. For lower face-lifting the surgeon makes these relatively small incisions only in the skin in front of the ears and under the chin. Forward and lifting force are then applied to the shaft of the device by the surgeon's hand to separate tissue planes while the shape of the device excludes critical structures (nerves, vessels) thus avoiding entanglement or trauma or indiscriminate cutting of these important structures. The same protrusions (in the most-preferred embodiment) that exclude critical structures by virtue of their relationship to the cutting recessed segments also serve to position the depth of the present invention with respect to the lower dermis. The spacing of the protrusions (bulbs) and recessions (lysing segments) maintains the tracking of the instrument. The beneficial feeling of "tracking" is instantly palpable by the surgeon on device motion and requires no monitor to know how the device is moving. Both the number and spacing of protrusions in one embodiment will aid in reducing wobble or lateral (horizontal) slippage during forward thrusting of the shaft. Vertical slippage is prohibited as well in one embodiment; the width of the protrusions/bulbs maintains the correct distance between the lysing/recessed segments and the delicate underside of the superficial skin or dermis. Beneficially, the tip of the device and the action of the device can be felt/appreciated without direct visualization (endoscope). The surgeon can palpably feel whether the device is tracking in the proper location; the feel of the device as it moves with palpable and easily grade-able resistance through the facial tissues can immediately tell the user the location and the amount of undermining that has occurred at that location.

Protrusions & Recession Embodiment

In this embodiment, the tip is comprised of alternating, but relatively symmetrical-across-a-midline, protrusions and recessions. The protrusions can be bulbous, geometric, etc., as long as the tips of the protrusions are able to push and compress tissues into the cutting recessed segments. The recessed segments should have a relatively sharp edge that effectively lyses the tissue that comes into contact as the device is pushed forward. The close spacing of the grooves (caused by the alternation of tip protrusions and recessions) provides the user with a feel during forced tissue movement and significantly limits slippage. The tip of the device, and the action of the device can be felt/appreciated without direct visualization (endoscope).

Laser-Energized Embodiment

In this embodiment laser light is transmitted from the laser to the hand piece and down the shaft and exits an optical window near the distal end of the shaft to heat the tissue that lies near the window. With the device positioned "window-up", the laser light will propagate away from the face to effectively heat the skin layer from the inside out. By selecting an appropriate laser wavelength, the laser penetration depth can be adjusted to control the thickness of heated tissue. For skin tightening, a $CO_2$ laser with a wavelength of 10 $\mu$m will deliver desirable results. Other usable lasers include erbium, holmium and neodymium. The purpose of the laser energy is to alter/irritate the collagen so as to controllably cause later shrinkage and to optionally control bleeding. For laser sources that are invisible to the human eye, the device may offer the user the option to simultaneously transmit visible light down the shaft to give the user the ability to visualize the region being treated. For example, red light that is easily transmitted through several millimeters of skin could be safely used to guide the surgeon. Laser irradiation can be controlled manually by the user or automatically to prevent excessive or inappropriate thermal damage.

Light Embodiment

In an alternative embodiment energized by polychromatic light, light is transmitted down or formed in the tip or the shaft and exits an optical window near the distal end of the shaft to heat the tissue that lies near the window. The purpose of the light energy is to alter/irritate the collagen so as to controllably cause later shrinkage and to optionally control bleeding. The light may contain wavelengths both visible and invisible to the human eye.

Temperature-Measuring Embodiment

In this embodiment (which may be combined with any of the other embodiments), the temperature of the target tissue is measured with a non-contact temperature sensor and the value displayed and used by the laser control unit to actively control the laser power. The temperature sensor can be an infrared temperature sensor, but other conventional sensors may be used, such as fiber optic fluorescence temperature sensors, and thermocouple sensors.

Low-Mid Frequency "Regular" Ultrasound-Energized Embodiment

In another energized embodiment in order to improve lysing efficiency, the device incorporates an ultrasound transducer into the hand piece that transmits ultrasound energy in the 3,000 Hz to 30,000 Hz range down the shaft to the tip. Vibrational energy registered/transferred in tissues surrounding the tip and any preplanned surface irregularities will be converted to tissue-altering heat that will contribute to facial tissue contraction.

High-Frequency Ultrasonic-Energized Embodiment

In another embodiment, high-frequency ultrasonic (10 MHz to 100 MHz) piezoelectric transducers may are located on upper and/or lower sides of the planes of the instrument preferably near to the tip. In one ultrasonic embodiment, piezoelectric ultrasonic transducers are usually located in the handle or lower shaft of the instrument.

Reciprocating Energy Embodiment

In another energized embodiment, in order to improve lysing efficiency, the device incorporates an electrically-driven or pneumatic-driven motor and gears in the hand piece to move the shaft and tip (in unison) at adjustable frequencies between 100 and 2,000 Hz with excursions (throws) varying from ½ mm to 2 cm. The motion of the surgeon's arm with these devices is expected to be <<1 Hz.

Electrosurgical/Radiofrequency-Energized Embodiment

In another embodiment, the recessed cutting segments of the device are energized by an electrosurgical RF generator to improve lysing and allow RF-heating of tissue. Electrosurgical/radiofrequency segments may also be located on upper and/or lower sides of the planes of the instrument preferably near to the tip.

Ionic Fluid/Electrosurgical-Energized "Arthrocare™" Embodiment

In a further embodiment, an ionic fluid may exude from more than one area that is in contact with underlying electrodes allowing passage of tissue-altering energy preferably near to the tip.

Thermal/Heating-Iron-Energized Embodiment

In an alternate embodiment, thermal or resistive elements may also be located on upper and/or lower sides of the planes of the instrument preferably near to the tip.

Microwave-Energized Embodiment

In a further embodiment, microwave-transmitting elements may also be located on upper and/or lower sides of the planes of the instrument preferably near to the tip.

The present invention can be used to improve the efficacy and safety of face-lifting and face-tightening and is thus useful in a variety of cosmetic procedures. The forgoing and other objects, features, and advantages of the present invention will become apparent from the following description and accompanying drawings.

Although in one embodiment, the shaft's cross-sectional shape is flat or planar, acceptable alternative versions of the shaft may be oval, circular, trapezoidal or geometric on cross-section. Although in one embodiment, the tip's shape has alternating protrusions and recessions, acceptable alternative versions of the tip shape may be semicircular, lenticulate or geometric. Alternatively, a non-energized protrusion-recession shaped tip may be used as well as other traditional instruments such as scissors to create the lift plane; this would be followed some time later, seconds to minutes, by the passage of a (non-tangentially) energized device lacking the tip shape.

BRIEF DESCRIPTION OF THE DRAWINGS

FIG. 2 is a side view of the face-lift apparatus 10.

FIG. 3 is an enlarged plan or top view of the tip 2 as used in upper face-lift.

FIG. 4 shows an off-center frontal view of the tip of face-lift apparatus protrusions and recessions.

FIG. 9A is an enlarged plan or top view of a high-frequency-ultrasound-energized face-lift apparatus 1200.

FIG. 9B is a side view of the of the high-frequency-ultrasound-energized face-lift apparatus 1200 showing elements identical to those in FIG. 9A in a different perspective.

FIG. 11 is a side view of the face-lift apparatus 110. The tip 102 may be slightly larger than the shaft 104 to which it is attached.

FIG. 12 is an enlarged plan or top view of the tip 102 as used in upper facelifts.

FIG. 13 is another enlarged plan or top view of a tip 102.

FIG. 14 is an enlarged partial cross section of a tip taken at 14—14 of FIG. 12.

FIG. 17 represents a top or plan view of the ionic fluid electrosurgical energized variant of the face-lifting device.

FIG. 18 represents a side view of the ionic fluid electrosurgical energized variant of the face-lifting device as shown in FIG. 18.

FIGS. 19A and B represent top views of the ionic fluid electrosurgical energized variant of the face-lifting device.

DETAILED DESCRIPTION OF THE INVENTION

The present invention provides a device that can be used by surgeons to provide quick and accurate face-lifting maneuvers that minimize the amount of tissue that has to be removed. The device is comprised of a hollow undermining shaft that can be easily positioned between dissection planes in tissue and then manipulated to separate tissue planes and lyse fibrous tissue. A laser light source and delivering means delivers energy to the distal end of the shaft. Embodiments of the invention provide a planar application of energy. A temperature sensor monitors the tissue temperature, and control electronics process temperature information to control the laser power for optimum tissue contraction. An optional secondary light source that is visible to the surgeon can be used to help visualize the location of the laser exit window. Optionally the device can also use ultrasound energy delivered down the shaft to improve tissue lysing.

Laser-Energized Embodiment

Figure 1:
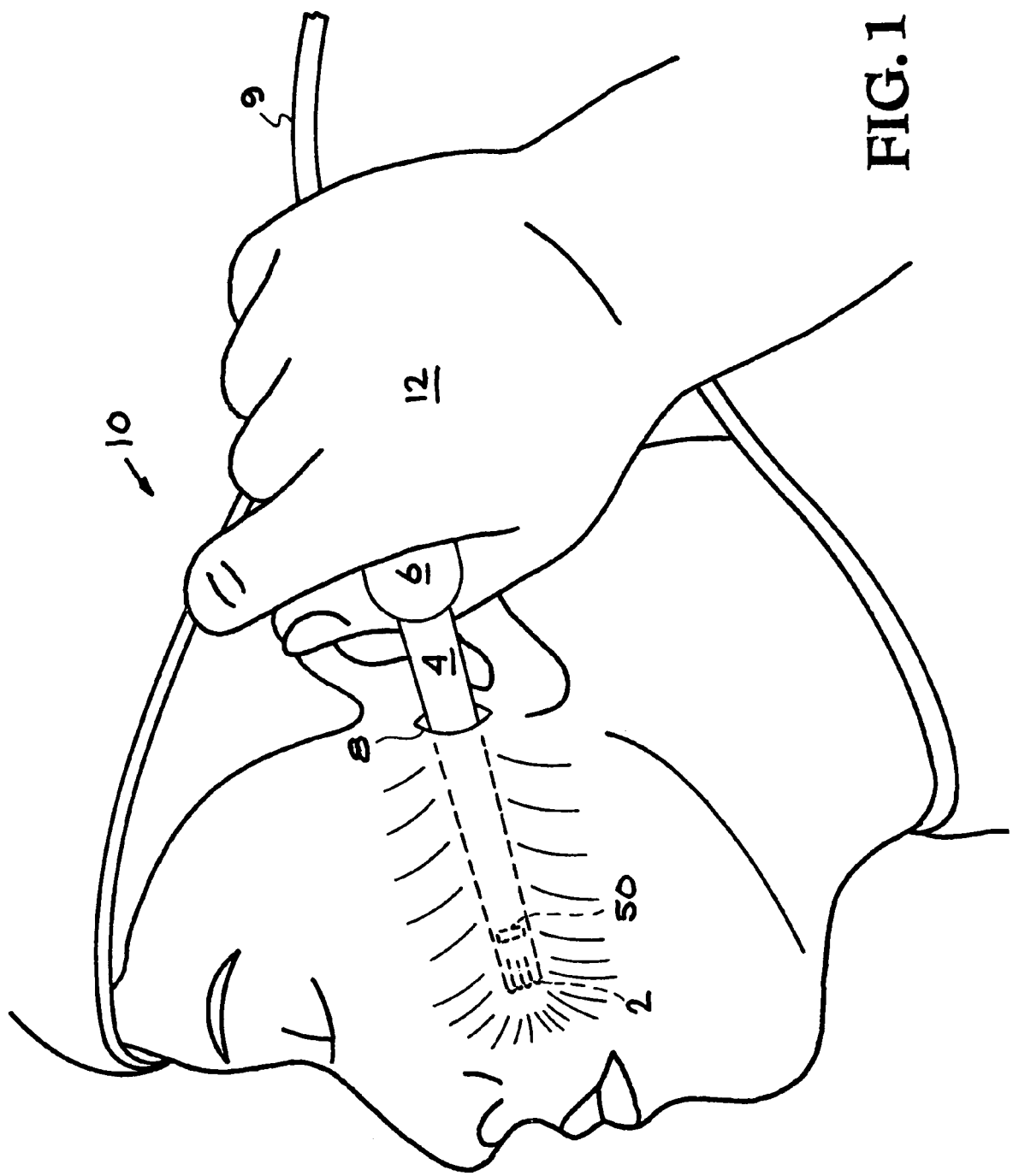
FIG. 1 shows a partial top view of the face-lift apparatus 10 of the present invention as it is being used.

FIG. 1 shows a partial top view of the face-lift apparatus 10 of the present invention as it is being used. The handle 6 of the apparatus 10 is gripped in the hand 12 of the user of the device. The shaft 4 with the special lysing tip 2 of the face-lift apparatus 10 is inserted through an opening 8 at a suitable location on the face of a patient. Dashed lines indicate the portion of the device hidden from view under the skin. Curved stretch lines indicate the upward force applied on the device 10 and shaft 4 and the overlying skin of the face. The apparatus may then be thrust forwardly while lifted forcefully by the operator to perform its function and maintain the plane of undermining. Window 50 (dashed and hidden from clear view in this representation) allows egress for laser light delivered to apparatus 10 via light delivery means contained in conduit 9. The conduit also contains the necessary electrical control wires necessary for device operation.

FIG. 2 is a side view of the face-lift apparatus 10. The tip 2 may be slightly larger than the shaft 4. The tip 2 can be a separate piece that is secured to shaft 4 by a variety of methods such as a snap mechanism, mating grooves, plastic sonic welding, etc. Alternatively, in this model tip 2 can be integral or a continuation of shaft 4 made of similar metal or materials. The tip 2 may also be constructed of materials that are both electrically non-conductive and of low thermal conductivity; such materials might be porcelain, ceramics or plastics. An optional electrically conductive element 61 brings RF electrosurgical energy to metal or electrically conductive elements mounted in the recessions (see FIG. 3). The shaft 4 is tubular in shape or can be a somewhat flattened tube oblong in cross section and possibly geometric as well. The shaft 4 is made of metal with a hollow interior that can contain insulated wire or wires 61. Alternatively, the shaft 4 may be made of plastic that will act as its own insulation about wire or electrically conductive element 61. The optional electrically conductive element 61 internal to shaft 4 conducts electrical impulses or RF signals from an optional external power/control unit (such as a Valleylab Surgistat, Boulder, Colo.). Hidden from this direct view located at the most proximal portion of the groove is electrically conductive element 81, powered by electrical source 18, which effects forward lysing and is located at the terminus of conductive element 61. An optional temperature sensor 35 (See FIG. 4) placed near the distal tip of the shaft is used to monitor the local temperature. This information can be used by the control electronics to control the energy delivered to the tip. An optional mid and low frequency ultrasound transducer 32 (See FIGS. 2 and 3) can also be activated to transmit energy to the tip 2 and provide additional heating and improve lysing.

FIG. 3 is an enlarged plan or top view of the tip 2 as used in upper face-lift. This tip 2 shows four protrusions 26 and three recessions 28. The groove created by the tapering recessions may be up to one centimeter in length. The width of this tip varies between 12 mm and 20 mm and the thickness varies between 3 mm and 4 mm. Optical window 50 allows laser light to exit the shaft and irradiate tissue directly above. A light delivery means which can be an optical fiber or hollow waveguide (such as metal-coated plastic manufactured by Polymicro Technologies, Inc of Phoenix, Ariz.) 52 is contained in conduit 9. The conduit 9 can also be an articulating arm as is commonly used in surgical laser systems. Additional control wires and power are delivered to the handpiece in the conduit 9. The user can enable or disable the laser through control switch 55. This embodiment may also include the current source 18 and electrodes 81 as shown in FIG. 2.

FIG. 4 shows an off-center frontal view of the tip of face-lift apparatus protrusions and recessions. The tip 2 has four protrusions 26 and three recessions 28 which optionally contain seated conductive elements 81. Window 50, possibly made of Germanium, allowing egress of laser light and collection of data by temperature sensor 35, are also located on the tip and may be of varying sizes. The width of this tip varies between 5 mm and 10 mm while the thickness may vary between 2 mm and 4 mm. The tip, however, is not constrained by those dimensions.

Figure 5:
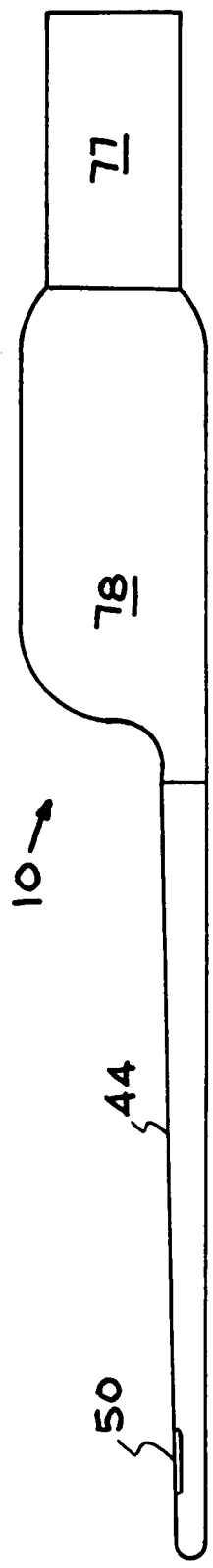
FIG. 5 is a side view of the present invention 10 with detachable handle 78 that fits over exogenous laser source.

FIG. 5 is a side view of the present invention 10 with detachable handle 78 that fits over exogenous laser source 77 such as a Sharplan Flashscanner or a Coherent Ultrapulse. The hollow section 44 of shaft 4 may act as a waveguide or may contain a metal-coated plastic fiberoptic or waveguide to allow laser light to move to and exit from window 50 near tip 2. Window 50 allows egress for laser light delivered to apparatus 10. Laser sources known to be usable in the present invention include both pulsed and continuous wave lasers such as $CO_2$, erbium YAG, Nd:YAG and Yf:YAG.

Figure 6:
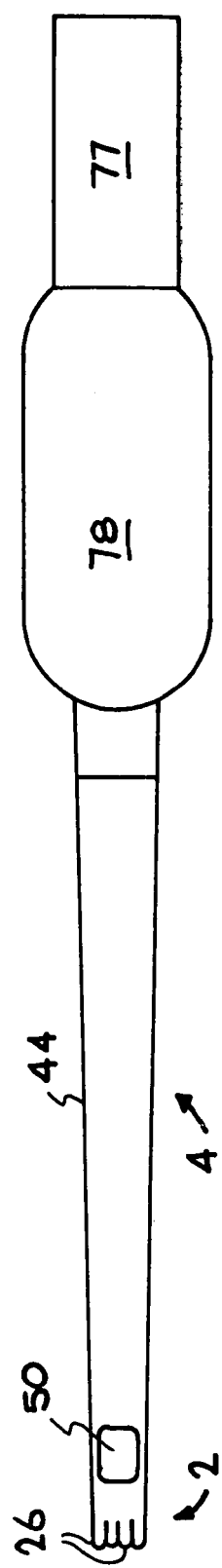
FIG. 6 is a top view of the present invention 10 with detachable handle 78 that fits over exogenous laser source.

FIG. 6 is a top view of the present invention 10 with detachable handle 78 that fits over exogenous laser source 77 such as a Sharplan Flashscanner or a Coherent Ultrapulse. Shaft 4 may act as a waveguide or may contain a metal-coated plastic fiberoptic or waveguide to allow laser light to move to and exit from window 50 that allows egress for laser light delivered to apparatus 10.

Figure 7:
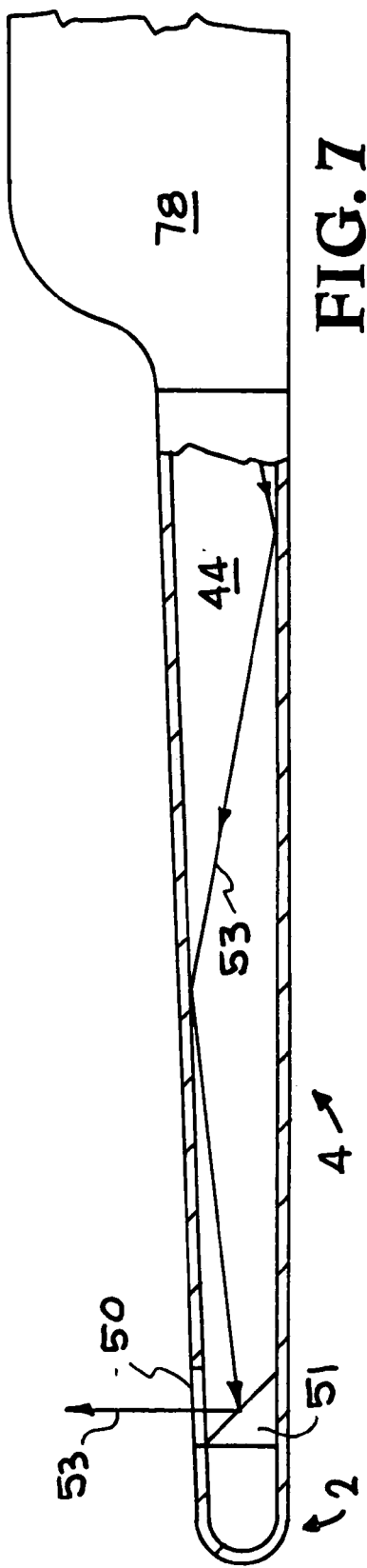
FIG. 7 is a cut-open side view of the present invention 10 with detachable handle 78 wherein shaft 4 acts as a waveguide 44 to allow laser light 53 to move to and exit from window 50.

FIG. 7 is a cut-open side view of the present invention 10 with detachable handle 78 wherein shaft 4 acts as a waveguide 44 to allow laser light 53 to move to and exit from window 50. An optical element 51 is used to reflect the laser light out through the window. In an alternative embodiment, the waveguide 44 formed by the internal surface of the shaft 4 is replaced by a one or multiple optical fibers or hollow fibers waveguides. The preferred light delivery means depends on the wavelength of the laser used. Infrared light emitted by the heated tissue can also be collected through the window and used by an infrared detector to measure the tissue temperature.

Non-Protrusion & Recession Embodiments

Figure 8A:
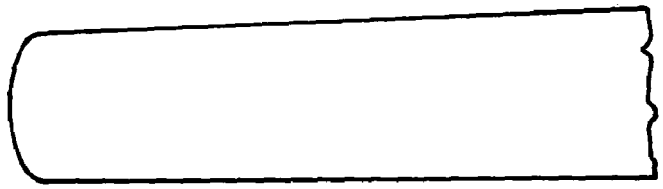
FIGS. 8A–F are enlarged plan or top views of several varieties of shapes of the tip as used in upper face-lift procedures.
Figure 8B:
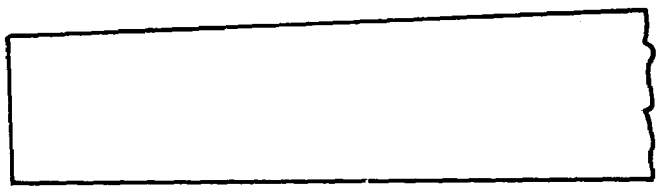
Figure 8C:
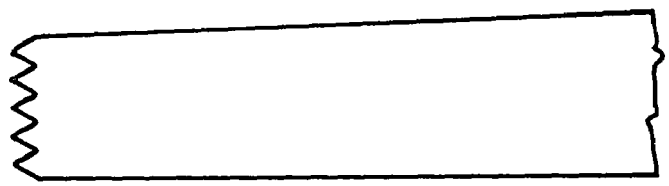
Figure 8D:
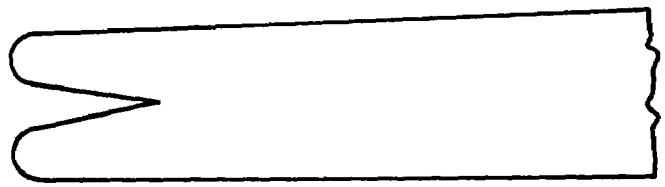
Figure 8E:
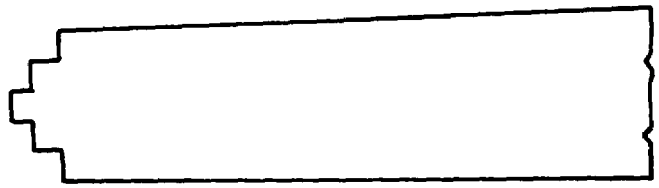
Figure 8F:
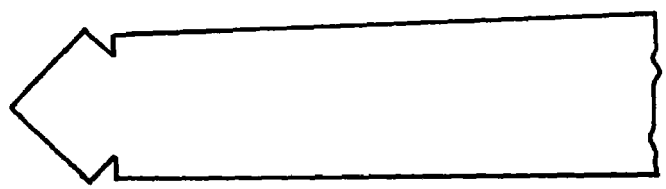

FIGS. 8A–F are enlarged plan or top views of several varieties of shapes of the tip as used in upper face-lift procedures. FIG. 8A shows an oval shaped-tip in this viewing angle. FIG. 8B shows a rectangular shaped-tip in this viewing angle. FIG. 8C shows a serrated shaped-tip in this viewing angle. FIG. 8D shows a grooved shaped-tip in this viewing angle. FIG. 8E shows a geometric shaped-tip in this viewing angle. FIG. 8F shows a diamond shaped-tip in this viewing angle. For whatever variety of tip is chosen, the customary size range of widths of these tips varies between 12 mm and 20 mm and the thickness varies between 3 mm and 4 mm. Adjacent or incorporated into the tip is the tissue-energizing area that allows the previously described forms of energy to cause tissue alteration directly above the path of the instrument High-Frequency Ultrasonic-Energized Embodiment FIG. 9A is an enlarged plan or top view of a high-frequency-ultrasound-energized face-lift apparatus 1200. The tip 1201 is secured to a shaft 1202 that may be tubular or flattened in cross-sectional shape. The shaft may be made of metal or plastic or ceramic and is connected to a plastic or polymer or ceramic tip section that is covered or coated with the piezo material "PZT" or "lead polymer" or PVDF that is "bonded in" and will transmit vibrational energy in the high range of ultrasound between 10 megahertz and 100 megahertz to the target tissues. When viewed from the top, the shape of the "bonded in" ultrasonic transducers 1209 will preferably be rectangular or geometric, however any number of imaginable shapes (for example ellipsoid, circle, hourglass, diamond, spade, heart, club, separate islands, etc.) may be used with elements individually or multiply bonded in the area. Electrical energy to power the "bonded in" ultrasonic transducers may be modulated or controlled by electronics 1203 located in the handpiece which are in turn electrified via electrical cord 1204 and further controlled via external control unit 1205 and attendant switch 1206. Alternatively, a switch 1208 may be present in the handle 1207 for easier controllability by the surgeon.

FIG. 9B is a side view of the of the high-frequency-ultrasound-energized face-lift apparatus 1200 showing elements identical to those in FIG. 9A in a different perspective. The design or configuration of the "bonded in" segment will most desirably be planar when viewed from the side and preferably be flush with the shaft or tip but may slightly protrude.

Reciprocating Energy Embodiment

Figure 10A:
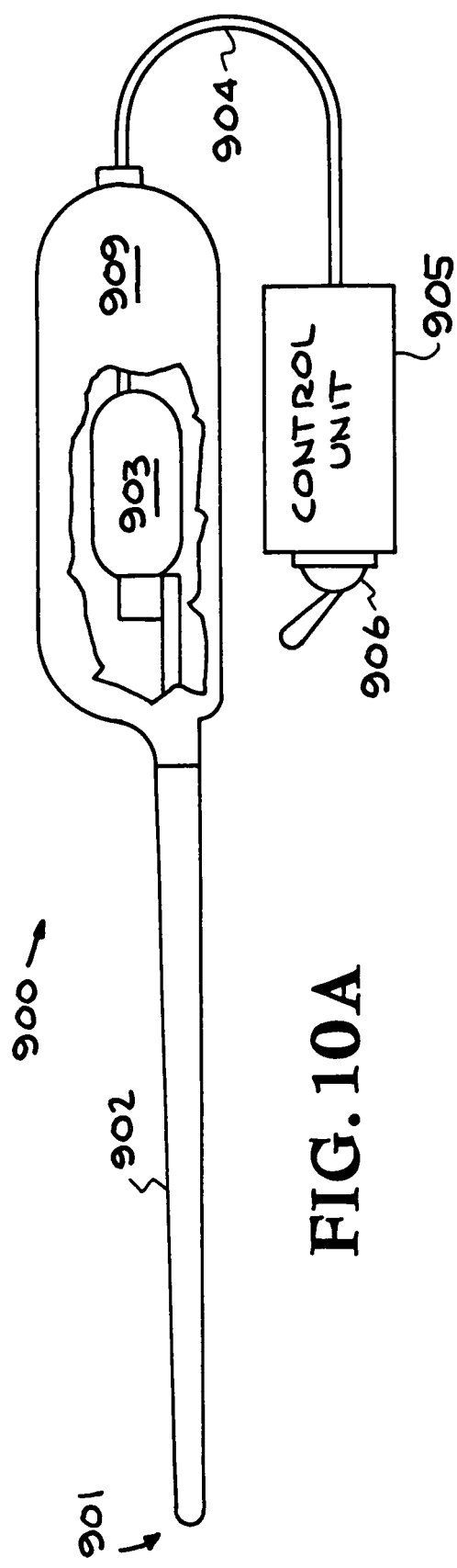
FIG. 10A is a side view of the electrically-driven-reciprocating face-lift apparatus 900.

An electrically-driven-reciprocating version of most of the energized face-lift devices can be made by combining the following designs in this section with the energized designs mentioned elsewhere in this manuscript FIG. 10A is a side view of the electrically-driven-reciprocating face-lift apparatus 900. The tip 901 is secured to shaft 902 that may be tubular or flattened in cross-sectional shape. The shaft may be made of metal or plastic that will conduct the kinetic energy in the form to forward/backward (to/fro) impulses of ½ mm to 2 cm generated by an insulated electrical motor 903 located in the handpiece 909 which is in turn electrified via electrical cord 904 and controlled via control unit 905 with switch 906.

Figure 10B:
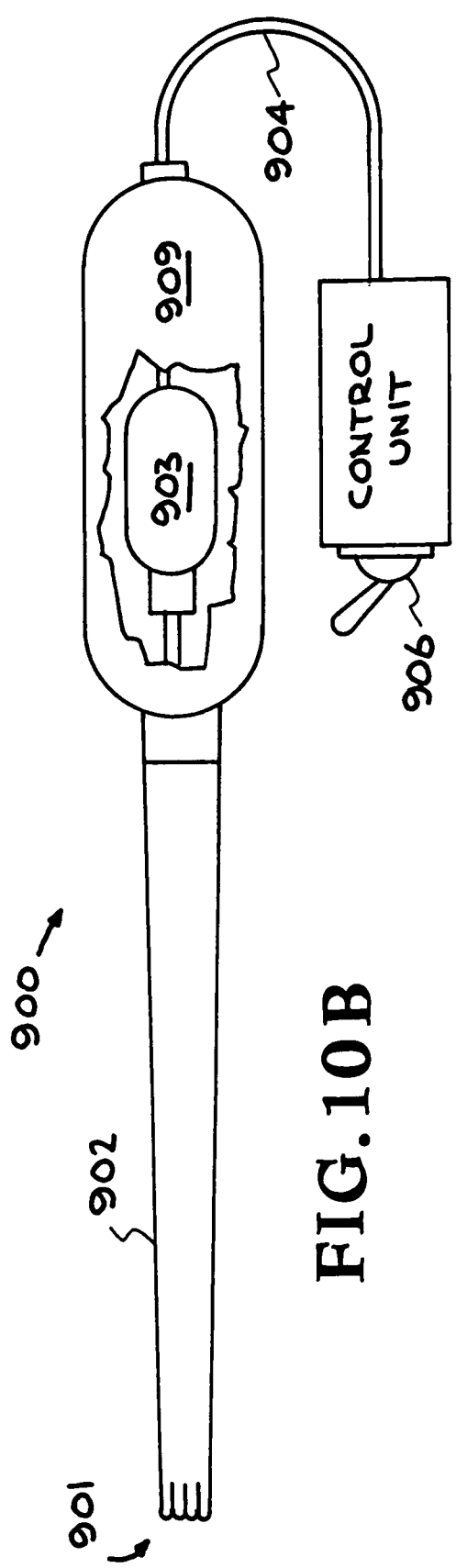
FIG. 10B is an enlarged plan or top view of the of the electrically-driven-reciprocating face-lift apparatus 900 showing elements identical to those in FIG. 10A in a different perspective.

FIG. 10B is an enlarged plan or top view of the of the electrically-driven-reciprocating face-lift apparatus 900 showing elements identical to those in FIG. 10A in a different perspective.

Figure 10C:
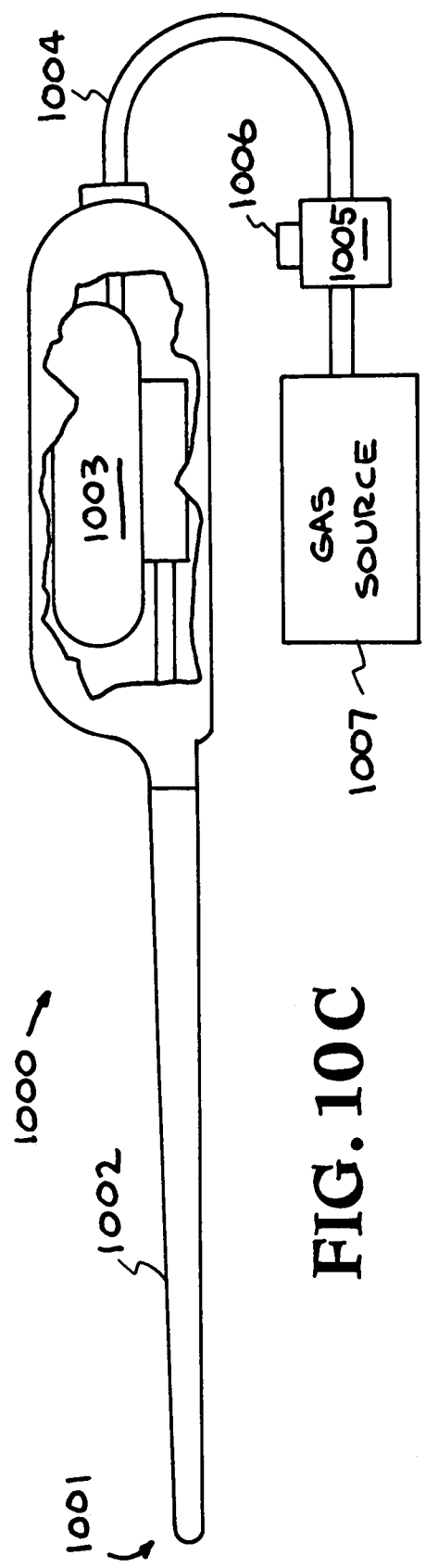
FIG. 10C is a side view of the pneumatically-driven-reciprocating face-lift apparatus 1000.

FIG. 10C is a side view of the pneumatically-driven-reciprocating face-lift apparatus 1000. The tip 1001 is secured to shaft 1002 that may be tubular or flattened in cross-sectional shape. The shaft may be made of metal or plastic that will conduct the kinetic energy in the form to forward/backward (to/fro) impulses of ½ mm to 2 cm generated by a pneumatic actuator 1003 located in the handpiece which is in turn pneumatically energized via gas conduit 1004 connecting to external pressurized gas source 1007 and controlled via control unit 1005 with switch 1006.

Figure 10D:
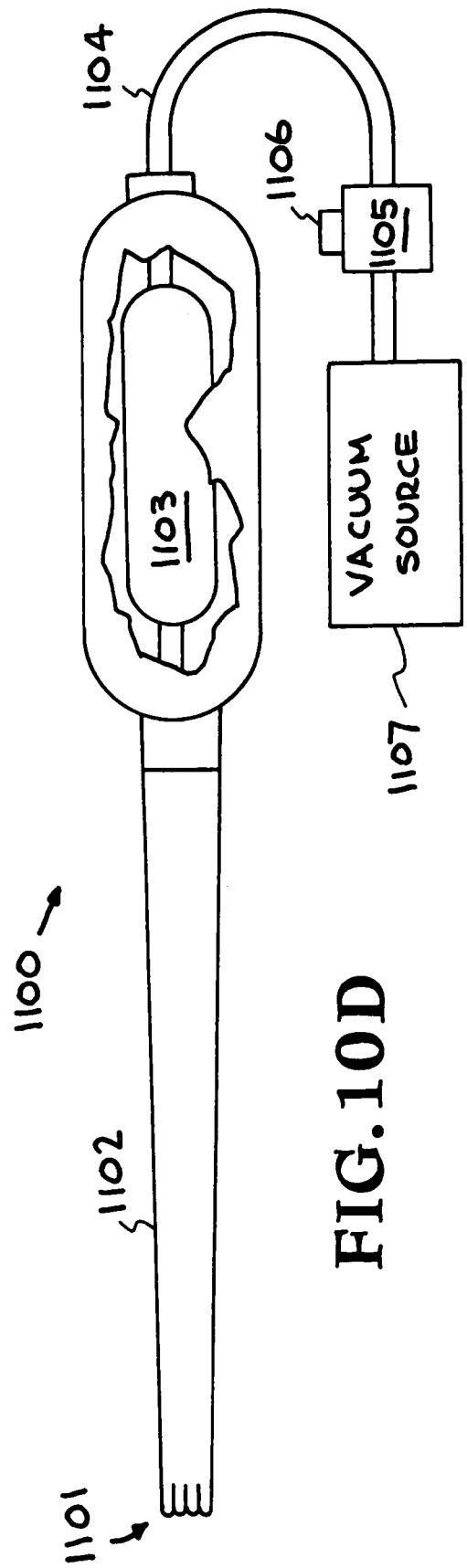
FIG. 10D is a side view of the suction-driven-reciprocating face-lift apparatus 1100.

FIG. 10D is a side view of the suction-driven-reciprocating face-lift apparatus 1100. The tip 1101 is secured to shaft 1102 that may be tubular or flattened in cross-sectional shape. The shaft may be made of metal or plastic that will conduct the kinetic energy in the form to forward/backward (to/fro) impulses of ½ mm to 2 cm generated by a suction-activated-actuator with flapper-valve 1103 located in the handpiece which is in turn suction-energized via gas conduit 1104 connecting to external vacuum source 1107 and controlled via control unit 1105 with switch 1106.

Electrosurgical/Radiofrequency-Energized Embodiment

FIG. 11 is a side view of the radiofrequency-energized face-lift face-lift apparatus 110. The tip 102 may be slightly larger than the shaft 104 to which it is attached. The tip 102 can be secured to shaft 104 by a variety of methods such as a snap mechanism, mating grooves, plastic sonic welding, etc. The tip 102 is constructed of materials that are both electrically non-conductive and of low thermal conductivity; such materials might be porcelain, ceramics or plastics. The shaft 104 is tubular in shape or can be a somewhat flattened tube oblong in cross section. The shaft 104 is made of metal with a hollow interior that will contain insulated wire or wires 116. Alternatively, the shaft 104 may be made of plastic that will act as its own insulation about wire or wires 116. The wires 116 internal to shaft 104 conduct electrical impulses or RF signals from an electrosurgical handpiece 118 located in handle 106. These impulses are transmitted from a electrosurgical handpiece 118 to the tip 102. Electrical energy is transmitted from an external generator (such as a Valleylab Surgistat, Boulder, Colo.) through standard wiring to the electrosurgical handpiece 118. In the embodiment shown here in FIG. 11, the shaft 104 is interlocked with the handle 106. The handle 106 has a recess into which an electrosurgical handpiece 118 may be installed. As previously stated, the electrosurgical handpiece 118 allows control of electrical or RF impulses sent to tip 102. The electrosurgical handpiece has a power control switch 120 to control its function. A male/female connector 124 makes the connection between the electrosurgical handpiece 118 and the wires 116. The electrosurgical handpiece 118 is secured in handle 106 by door 122. The electrosurgical handpiece 118 receives its power from an external source or electrosurgical generator (source not shown in the figure). A temperature sensor 135 is placed near the energized section of the tip to monitor tissue temperatures in order to create feedback or audible output to the surgeon or a computer so as to controllably reduce the amount of radiofrequency or ultrasonic energy applied to the target tissues.

FIG. 12 is an enlarged plan or top view of the tip 102 as used in upper face-lifts. This tip 102 shows five protrusions 126 and four recessions 128. The groove created by the tapering recessions may be noticeable up to one centimeter in length. The width W of this tip varies between 12 mm and 20 mm and the thickness varies between 3 mm to 4 mm. The tip, however, is not constrained by those dimensions. Also shown in FIG. 12 are the conductors 130 that transmit the signals supplied by wire 116 from electrosurgical handpiece 118 to tip 102. Connection between conductors 130 embedded in tip 102 and wires 116 in shaft 104 is made at the time tip and shaft are joined.

FIG. 13 is another enlarged plan or top view of a tip 102. This tip has three protrusions and two recessions and is the tip design used in lower face-lift. The width W of this tip varies between 5 mm and 10 mm while the thickness remains similar to the tip of FIG. 12 at 2 mm to 3 mm. This tip, however, is not constrained by those dimensions. Shown also are the conductors 130 for bringing power to the tip.

FIG. 14 is an enlarged partial cross section of a tip taken at 14—14 of FIG. 12. Here is shown the relationship between the protrusions 126 and the recessions 128. Also illustrated is the conductor 130.

Figure 15:
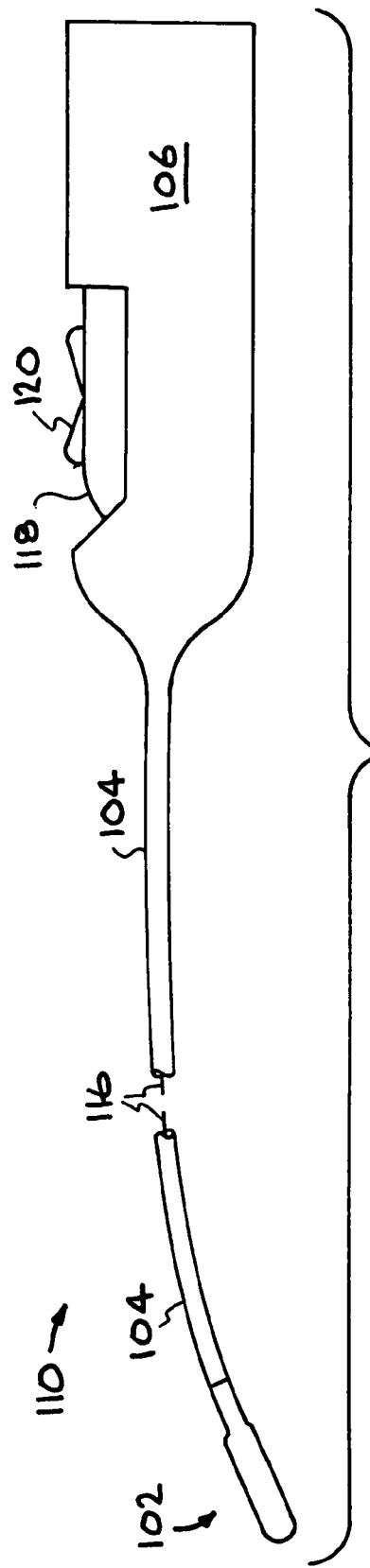
FIG. 15 is an illustration of a face-lift apparatus.

FIG. 15 is an illustration of a face-lift apparatus similar to those previously described. This apparatus differs in that shaft 104 is constructed of a material that allows shaft 104 to have some flexibility. This may reduce the stress to some patient's delicate skin during use. The shaft 104, however, must have enough rigidity to enable the operator to maintain control over positioning the tip 102.

Figure 16:
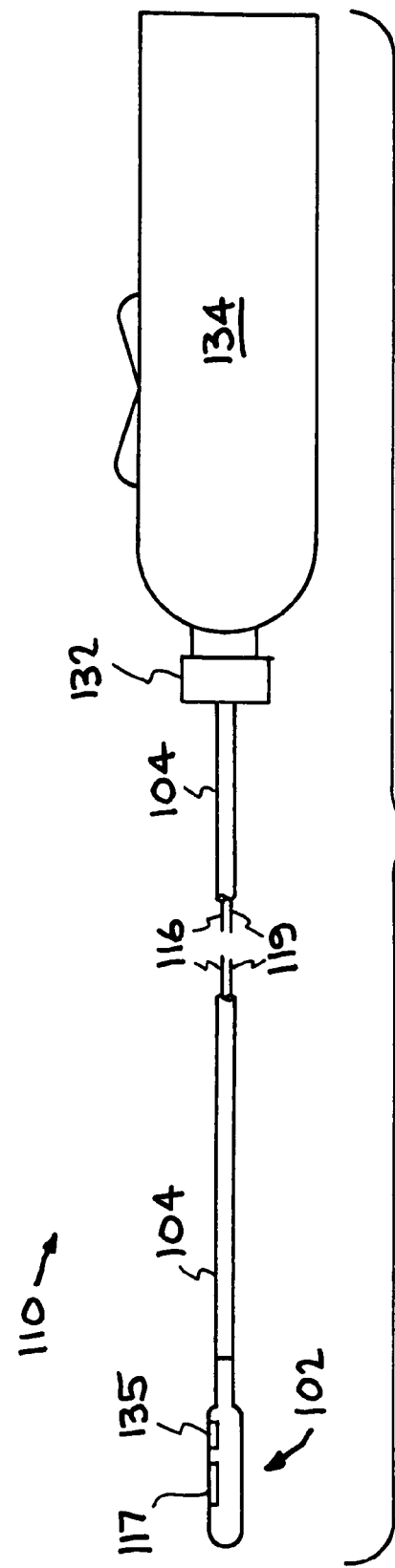
FIG. 16 is a face-lift apparatus where the electrosurgical handpiece 118 and handle 106 have been combined to form integral unit 134.

FIG. 16 is a face-lift apparatus again similar to those previously described but differing in that the electrosurgical handpiece 118 and handle 106 have been combined to form integral unit 134. An optional and additional feature in the handle or hand-piece can be an ultrasonic piezoelectric transducer 132 that sends ultrasonic energy to the tip 102 of the face-lift device. The wire 116 would need to be replaced by a small metal shaft to conduct the ultrasonic energy. The shaft may be specially insulated or coated (e.g., with Teflon) to protect surrounding tissue. Alternatively, to clear debris and to enhance efficiency, a motor capable of lower vibrational energy may be incorporated into handle 34. Furthermore, uniform tissue heating element 117 may be incorporated on one side of the proximal tip and connected to insulated conductive element 119 passing through the shaft 104. Conductive element 119 and thus heating element 117 are controllably electrified at handle 134. It is noteworthy that radiofrequency uniform tissue heating element 117 (that may be located on a side of the proximal tip or shaft) is distinct and separate from the radiofrequency elements located in the lysing areas of the tip. It is also noteworthy that uniform tissue heating element 117 may be controlled in a fashion independent from the radiofrequency elements in the lysing segments. A temperature sensor 135 is placed near the energized section of the tip to monitor tissue temperatures in order to create feedback or audible output to the surgeon or a computer so as to controllably reduce the amount of radiofrequency or ultrasonic energy applied to the target tissues. This loop may thus controllably restrict thermal tissue damage and optimize contraction results. The temperature sensor 135 may be of an infrared type, optical fiber type, an electronic type, or optical fluorescence type, each being known in the prior art and thus a detailed description thereof is deemed unnecessary.

Ionic Fluid/Electrosurgical-Energized "Arthrocare™" Embodiment

FIG. 17 represents a top or plan view of the ionic fluid electrosurgical energized variant of the face-lifting device. The electrosurgical version of the face-lift device may be modified such that several sets of anodes 1303 and cathodes 1304 are placed in relatively proximal locations at the end of the shaft 1301 or upon the tip 1302. This modification will result in an ionic fluid version 1300 of the electrosurgical-energy embodiment. One or more sets of electrodes 1303 and 1304 are placed in proximity to separate holes 1305 and 1306 that allow the passage of ionic fluids able to conduct electrical energy into the adjacent target tissue. The ionic fluids are brought into the shaft via individual conduits 1307 and 1308 that split off from the fluid source 1309 at point 1310 which may be proximal to or distal to the handle 1311. FIG. 18 represents a side view of the ionic fluid electrosurgical energized variant of the face-lifting device as shown in FIG. 17.

FIGS. 19A and B represent top views of the ionic fluid electrosurgical energized variant of the face-lifting device. Specifically, the shape of the pattern 1312 of the multiplicity of drilled holes in the shaft or tip may be rectangular or geometric, however any number of imaginable shapes (for example ellipsoid, circle, hourglass, diamond, spade, heart, club, separate islands) may be used to transmit energy to the target tissues. The shaft and tip may be insulated with materials such as Teflon®.

Thermal/Heating-Iron-Energized Embodiment

Figure 20:
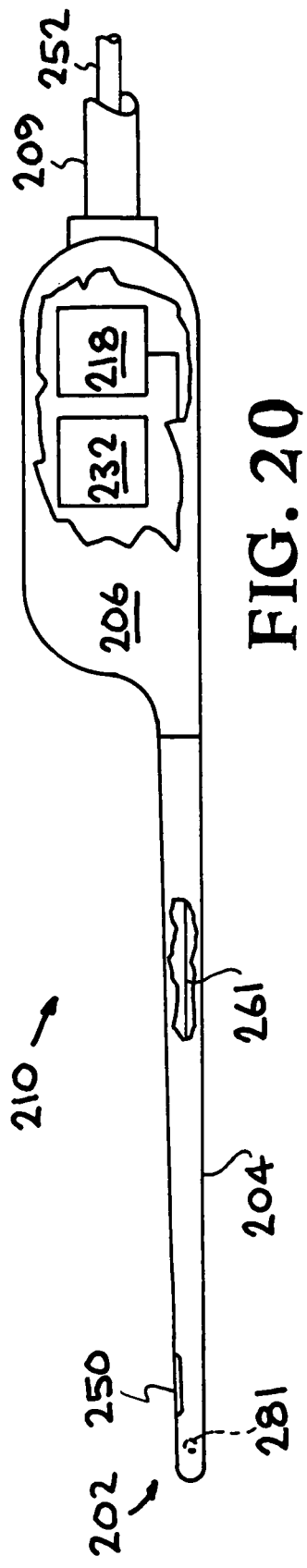
FIG. 20 is a side view of the face-lift apparatus 210.

FIG. 20 is a side view of the face-lift apparatus 210. Window 250 (dashed and hidden from clear view in this representation) allows thermal energy to escape from within the shaft 204. The tip 202 may be slightly larger than the shaft 204. The tip 202 can be a separate piece that is secured to shaft 204 by a variety of methods such as a snap mechanism, mating grooves, plastic sonic welding, etc. Alternatively, in this model tip 202 can be integral or a continuation of shaft 204 made of similar metal or materials. The tip 202 may also be constructed of materials that are both electrically non-conductive and of low thermal conductivity; such materials might be porcelain, ceramics or plastics. Portions of the tip and shaft may be covered with Teflon to facilitate smooth movement of the device under the skin. An optional electrically conductive element 261 may be provided to bring RF electro surgical energy from RF source 218 to metal or electrically conductive elements mounted in the recessions (see FIG. 21). The shaft 204 is tubular in shape or can be a somewhat flattened tube oblong in cross section. The shaft 204 is made of metal with a hollow interior that can contain insulated wire or wires 261. Alternatively, the shaft 204 may be made of plastic that will act as its own insulation about wire or electrically conductive element 261. The optional electrically conductive element 261 internal to shaft 204 conducts electrical impulses or RF signals from an optional external power/control unit (such as a Valleylab Surgistat, Boulder, Colo.). An optional temperature sensor 235 placed near the distal tip of the shaft is used to monitor the local temperature. This information can be used by the control electronics to control the energy delivered to the tip. An ultrasound transducer 232 can also be activated to transmit energy to the tip 202 and provide additional heating and improve lysing.

Figure 21:
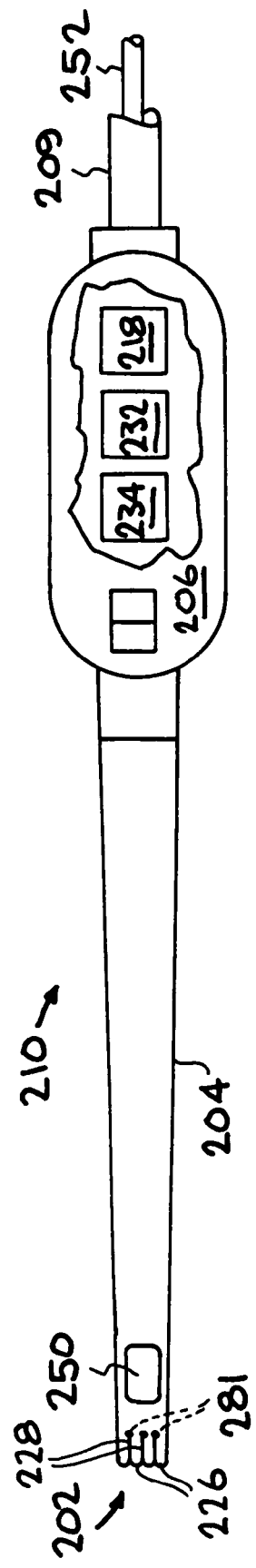
FIG. 21 is an enlarged plan or top view of the tip 202 as used in upper facelift.

FIG. 21 is an enlarged plan or top view of the tip 202 as used in an upper face-lift or brow lift. This tip 202 shows four protrusions 226 and three recessions 228. The groove created by the tapering recessions may be up to one centimeter in length. The width of this tip varies between 12 mm and 20 mm and the thickness varies between 3 mm and 4 mm. Optical window 250 allows thermal radiation to exit the shaft and irradiate tissue directly above the window. The user can enable or disable the thermal source through a hand or foot switch (not shown).

Figure 22:
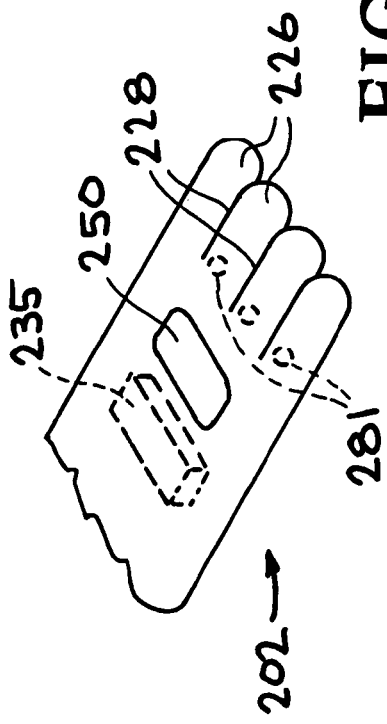
FIG. 22 shows an off-center frontal view of the tip of the face-lift apparatus protrusions and recessions.

FIG. 22 shows an off-center frontal view of the tip of the face-lift apparatus protrusions and recessions. The tip 202 has four protrusions 226 and three recessions 228 in which are seated electrodes 281. The RF electrodes 281 located at the most proximal portion of the cutting recessions can increase lysing and coagulation at the cutting edge. The RF electrodes 281 are connected by conducting wires 261 (FIG. 22) to the power/control unit. The user can enable or disable the RF power through a hand or foot switch (not shown). Window 250, allowing egress of thermal radiation and temperature sensor 235 are also located on the tip and may be of varying sizes. The width of this tip varies between 5 mm and 10 mm while the thickness may vary between 2 mm and 4 mm. The tip, however, is not constrained by those dimensions.

Figure 23:
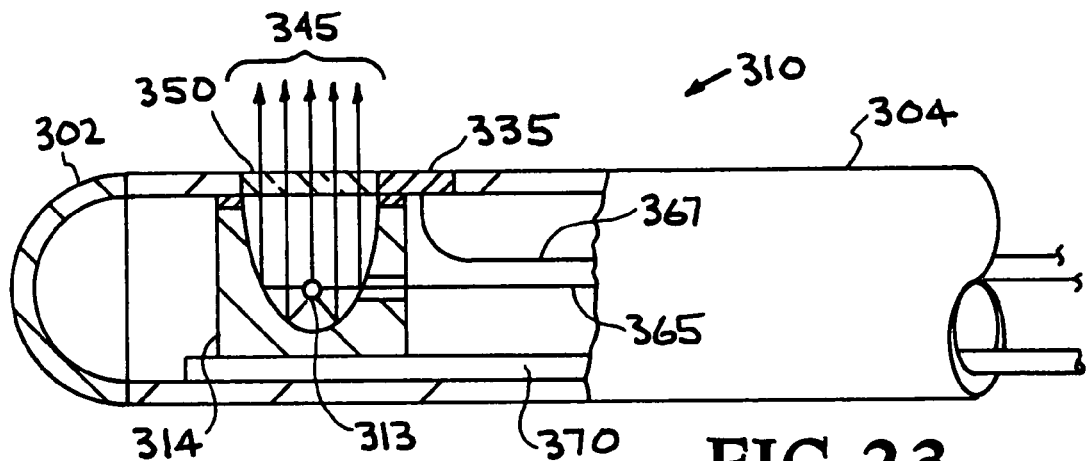
FIG. 23 shows a cross sectional view of an embodiment of the face-lift device 210 of the present invention.

FIG. 23 shows a cross sectional view of an embodiment of the face-lift device 310 of the present invention. The shaft 304 with the special lysing tip 302 is inserted through an opening at a suitable location on the face of a patient. The apparatus may then be thrust forwardly while lifted forcefully by the operator to perform its function and maintain the plane of undermining. A hot filament 313 within the device is heated by flowing current through connecting wires 365.

The filament 313 is held rigidly in position within the parabolic cavity by the strength of the wire 365. Alternately, the filament 313 is fixedly attached to the shaft 304. The hot filament 313 emits optical and thermal radiation 345 that can directly exit window 350 or be reflected off a reflector 314 to also exit through window 350. The reflector 314 can have a parabolic shape to effectively collect all optical and thermal radiation emitted away from the window 350. The hot filament 313 can be a tungsten carbide filament similar to those used in high power light bulbs. The wavelength may be adjusted and controlled by adjusting the filament temperature/current. The window 350 can be selected from a wide variety of glass that transmits optical, near infrared and infrared light (e.g., quartz, fused silica and germanium.) The tissue penetration depth depends on the wavelength of the light (e.g., 1 $\mu$m penetrates through 10 mm, 10 $\mu$m penetrates through 0.02 mm). The broad emission spectrum from the hot filament 313 can be filtered by window 350 to achieve the desired tissue effect. In particular filtering the emission spectrum to heat the dermis to temperatures of approximately 70° C. will cause the desired collagen shrinkage and tightening. The optimum spectral filtering depends on skin thickness and structure. A temperature sensor 335 connected to the control unit by electrical wire 367 monitors the temperature of tissue that is in contact with the shaft 304. In order to eliminate excessive heating of the shaft 304 and the surrounding facial tissue, the heating element 313 and reflector 314 are thermally isolated by low thermal conductivity materials. The heating element is isolated by not touching the shaft, whereas the reflector can have an isolating layer where it attaches to the shaft. In addition, cold nitrogen gas can be injected through tube 370 and pumped out through the hollow shaft to cool the tip 302 and shaft 304. Flowing nitrogen gas (or another inert gas) through the hollow shaft also reduces oxidation damage to the filament.

Figure 24:
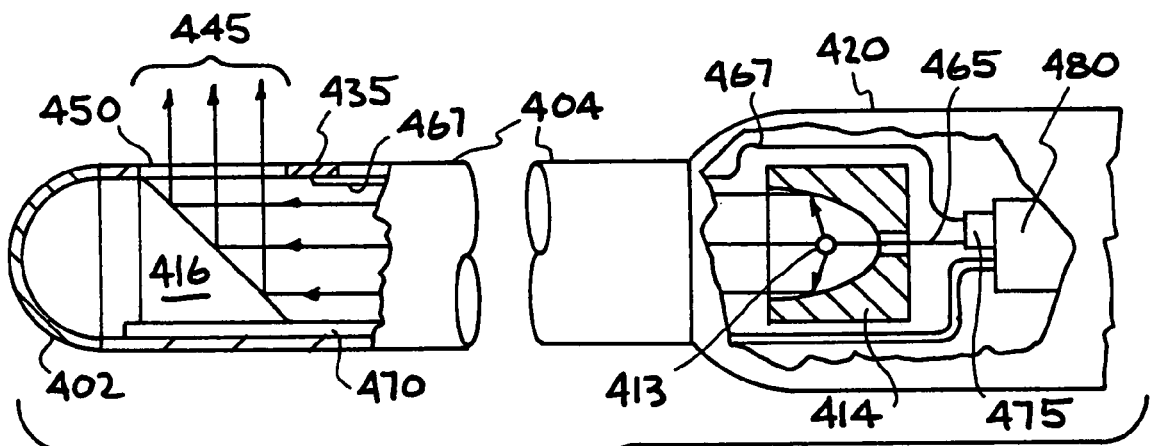
FIG. 24 shows an alternative embodiment of the present invention that reduces the thermal load to the shaft.

FIG. 24 shows an alternative embodiment of the present invention that reduces the thermal load to the shaft 404 and eliminates the need for high electrical currents within the shaft. In this embodiment the hot filament 413 is located in the handle 420 of the device and is connected to the power unit by wires 465 and cable 475. The optical and thermal radiation 445 is transported through the hollow wave-guide within the shaft 404 and reflected off the mirror 416 through the window 450. The absorption coefficient within the wave-guide is inversely proportional to the cube of the height of the hollow wave-guide within the shaft and can be made small for the hot filament 413 when operated at temperatures greater than 600 degrees. The absorbed energy would be evenly distributed over the entire shaft 404 and the average temperature increase would be small. A mirror reflector 414 redirects radiation emitted away from the shaft down the shaft to improve overall system efficiency. A temperature sensor 435 connected to the control unit by electrical wire 467 and cable 475 monitors the temperature of tissue that is in contact with the shaft 404. The ability to continuously monitor the temperature greatly reduces the danger of overheating and tissue carbonization. In addition, cold nitrogen gas can be injected through tube 470 to cool the tip 402 and shaft 404. The nitrogen gas can exit through the handle 420 or be recirculated through a cooling system. Flowing nitrogen gas through the hollow shaft also reduces oxidation damage to the filament. A cable 480 connects the present device to the control/power unit.

Figure 25:
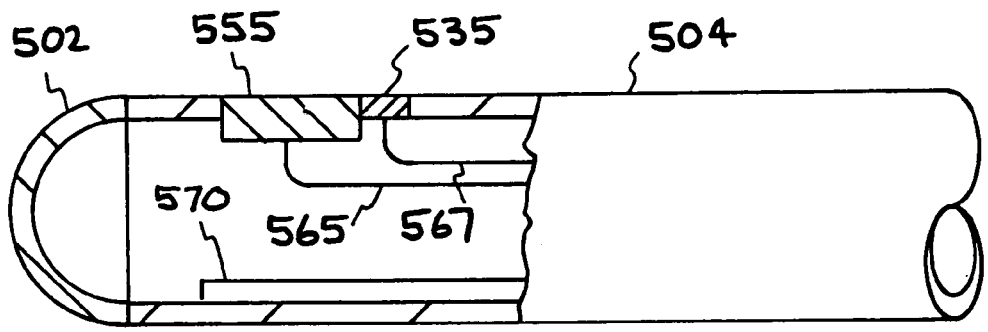
FIG. 25 shows an alternative embodiment of the present invention in which tissue heating is achieved by the direct contact with a hot surface.

FIG. 25 shows an alternative embodiment of the present invention in which tissue heating is achieved by the direct contact with a hot surface 555. In this embodiment electric current flowing through wires 565 heat a resistive load 555 to a user selected temperature. For most applications the temperature will be less than 80° C. to induce collagen shrinkage but prevent thermal collateral damage. This embodiment eliminates the risk that any tissue region can be heated above the desired temperature by misuse. This allows the size of the hot surface 555 to be larger (e.g. several centimeters long, 1 centimeter wide) which can speed up the procedure. In addition, the hot surface 555 can be made up of multiple elements that can be set to different desired temperatures. The resistive load could be a thin film resistor and the film temperature could be estimated from the measured resistance. Alternatively a separate temperature sensor 535 can be placed close to the heating element. The measured temperature is used by the control unit to control the current through the resistive load. In order to reduce heating to the shaft 504 and tip 502, cold gas or liquid can be injected through tube 570 and pumped out through the hollow shaft. The specific shape of the heater 555 and surface temperature can be adjusted to obtain the desired tissue coagulation depth. Instead of a resistive load, the heating element could be the hot side of a Peltier thermoelectric cooler. An advantage of a thermoelectric cooler is that the opposite surface is cooled below ambient temperature. Single stage thermoelectric coolers can achieve temperature differences of up to 40° C. By thermally connecting the cold surface of the thermoelectric cooler to the bottom of the shaft the cooler can be used to reduce heating of the shaft away from the hot surface.

In all embodiments of the device the shaft can be coated with a biocompatible non-stick material such as Teflon® to reduce tissue sticking to the device during the procedure.

Microwave-Energized Embodiment

Figures 26, 27:
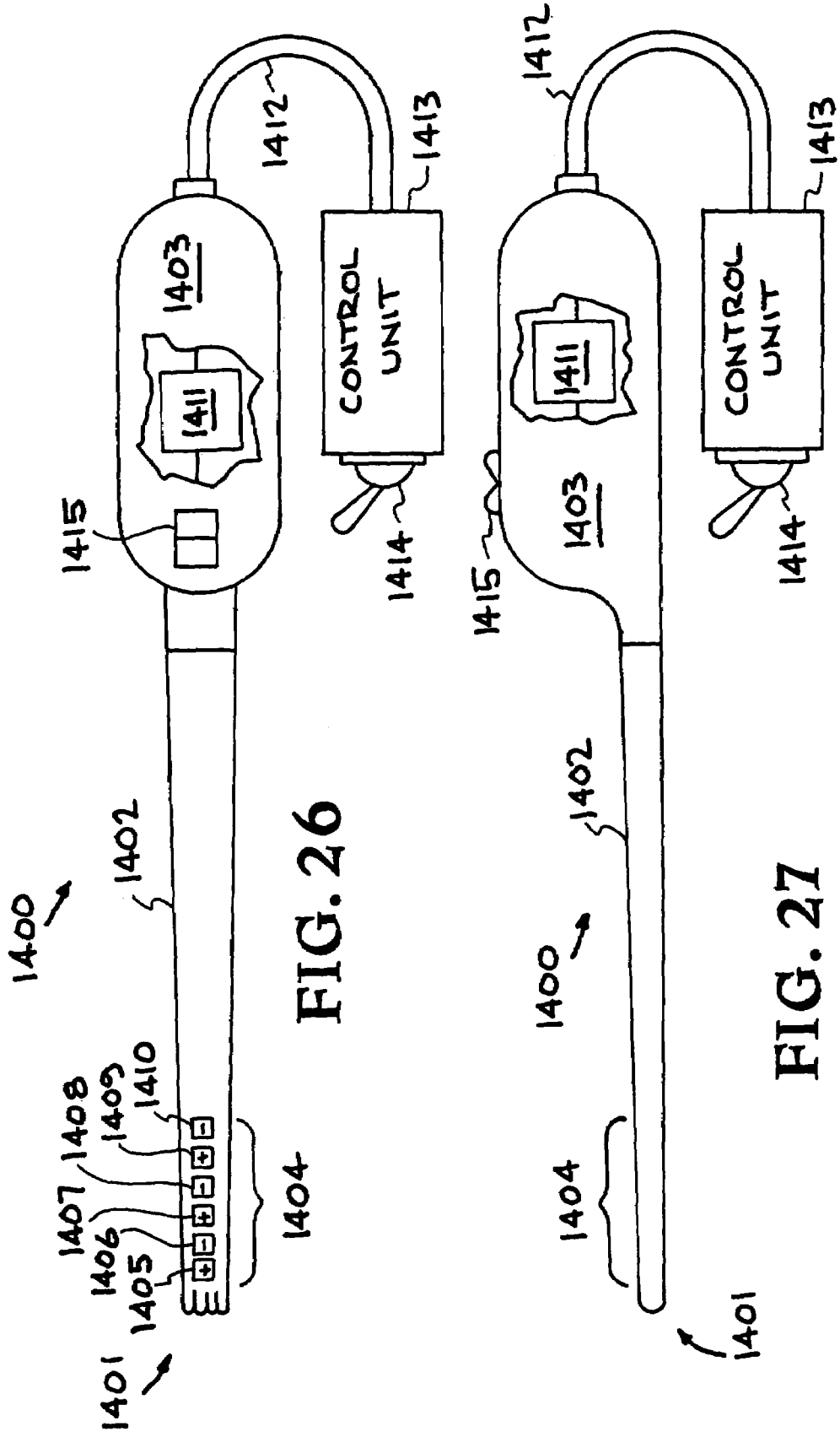
FIG. 26 is an enlarged plan or top view of a microwave-energized face-lift apparatus 1400.
FIG. 27 is a side view of the of the microwave-energized face-lift apparatus.

FIG. 26 is an enlarged plan or top view of a microwave-energized face-lift apparatus 1400. The tip 1401 is secured to shaft 1402 that may be tubular or flattened in cross-sectional shape; the shaft is further attached to handle 1403. The shaft may be made of metal or plastic or ceramic is connected to a plastic or polymer or ceramic tip section that has an even total number of phased array antennas 1404 attached or exposed on a planar or relatively planar or slightly curviform side. The phased array of antennas is made of metal (preferably stainless steel, aluminum, gold, steel, or platinum). The phased array is able to function in the range of 1 to 10 gigahertz yielding up to 20 watts of power with a depth of penetration of 1–3 mm. Opposing signs 1405, 1406, 1407, 1408, 1409, and 1410 are placed adjacent to control the depth of tissue penetration of microwave energy. Phases of electromagnetic field in different elements are fixed. Electric fields cancel at distance but allow and effect to nearby tissue. When viewed from the top the shape of the phased array of antennas will preferably be rectangular or geometric, however any number of imaginable shapes (for example ellipsoid, circle, hourglass, diamond, spade, heart, club, separate islands). Electrical energy to power the phased array of antennas may be modulated or controlled by electronics 1411 located in the handpiece which are in turn electrified via electrical cord 1412 and further controlled via external control unit 1413 and attendant switch 1414. Alternatively, a switch 1415 may be present in the handle 1403 for easier controllability by the surgeon.

FIG. 27 is a side view of the of the microwave-energized face-lift apparatus 1400 showing elements identical to those in FIG. 26 in a different perspective. The design or configuration of the "phased array" 1404 will most desirably be planar when viewed from the side and preferably be flush with the shaft or tip but may slightly protrude.

The foregoing description of preferred embodiments of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

We claim:

1. An apparatus, comprising:
   a shaft having a proximal end and a distal end; and
   a plurality of protruding members fixedly attached on said distal end of said shaft, wherein said plurality of protruding members are positionally fixed relative to said shaft, wherein each protruding member of said plurality of protruding members is positionally fixed relative to any other protruding member, wherein said plurality of protruding members comprises a first protruding member and a second protruding member; and
   a lysing mechanism comprising a first electro-conductive lysing segment located between said first protruding member and said second protruding member, wherein said lysing segment is configured to cut on its distal side,
   wherein said plurality of protruding members is insulated from said lysing mechanism, wherein said plurality of protruding members define a first plane on one side of said lysing mechanism and further define a second plane on the side of said lysing mechanism that is opposite to that of said first plane, wherein said lysing mechanism is fixed in a location substantially parallel to and within the range extending from said first plane and said second plane, wherein said apparatus is configured to cut two opposing and substantially planar tissue planes that are parallel with said first plane and said second plane as said apparatus is pushed through tissue.

2. The apparatus of claim 1, further comprising means for controlling the heating of said shaft.

3. The apparatus of claim 2, wherein said means for controlling the heating of said shaft comprises means for flowing an inert gas through said shaft.

4. The apparatus of claim 3, wherein said means for flowing an inert gas through said shaft comprises means for flowing cold nitrogen.

5. The apparatus of claim 1, wherein said shaft comprises material selected from a group consisting of porcelain, ceramic and plastic.

6. The apparatus of claim 1, further comprising an ultrasound transducer within said shaft, wherein said ultrasound transducer is operatively connected near said distal end for providing ultrasound energy to said tissue.

7. The apparatus of claim 1, further comprising means for providing radio frequency energy to said lysing mechanism to improve tissue lysing and provide tissue heating.

8. The apparatus of claim 1, wherein said distal end is attached to said shaft by a mechanism selected from a group consisting of a snap mechanism, mating grooves and a plastic sonic weld.

9. The apparatus of claim 1, wherein said shaft comprises material that is both electrically non-conductive and of low thermal conductivity.

10. The apparatus of claim 1, wherein at least one protruding member of said protruding members has an opening at said distal end.

11. The apparatus of claim 10, further comprising at least one lumen extending through at least a portion of said shaft and terminating at said opening.

12. The apparatus of claim 11, wherein said at least one lumen is attached to a vacuum source.

13. The apparatus of claim 1, further comprising means for delivering ultrasonic energy to the distal end of the shaft.

14. The apparatus of claim 13, further comprising control means for controlling the delivery of said energy to said distal end of said shaft.

15. The apparatus of claim 14, further comprising a temperature sensor that senses the temperature at said distal end of said shaft, wherein said sensor sends a signal to said control means, and wherein said control means controls the delivery of said energy to said distal end to adjust the temperature.

16. The apparatus of claim 1, wherein the thickness of said distal end of said shaft is less than about 1 cm and the width of said distal end is less than about 2 cm.

17. The apparatus of claim 1, further comprising a temperature sensor fixedly connected to said shaft, wherein said temperature sensor is operatively connected near said distal end of said shaft to monitor tissue temperature.

18. The apparatus of claim 17, further comprising control electronics that process said tissue temperature to control said radiation for optimum tissue contraction.

19. The apparatus of claim 18, further comprising a user interface operatively connected to said control electronics.

20. The apparatus of claim 19, wherein said user interface comprises a touch pad.

21. The apparatus of claim 17, wherein said temperature sensor is selected from a group consisting of an infrared temperature sensor, a fiber optic fluorescence temperature sensor, a thermal resistance sensor and a thermocouple sensor.

22. The apparatus of claim 1, further comprising means connected to said shaft for providing energy to targeted tissue.

23. The apparatus of claim 22, wherein said means for providing energy comprises means for providing radiofrequency radiation.

24. The apparatus of claim 22, wherein said means connected to said shaft for providing energy to targeted tissue include means for providing energy in a plane.

25. The apparatus of claim 22, wherein said means for providing energy comprises means for providing thermal radiation.

26. The apparatus of claim 25, wherein said means for providing thermal radiation includes an optical window in said shaft, wherein said optical window is operatively positioned for transmitting thermal radiation to said tissue.

27. The apparatus of claim 25, wherein said means for providing thermal radiation comprises a segment that may be heated, wherein said segment is located near said distal end of said shaft and connected to said shaft, wherein said segment can heat tissue directly.

28. The apparatus of claim 27, wherein said segment comprises a thin film resistor, wherein said apparatus further comprises means for flowing a current through said thin film resistor.

29. The apparatus of claim 25, wherein said means for providing thermal radiation comprises a filament.

30. The apparatus of claim 16, further comprising a reflector operatively positioned near said filament to effectively reflect optical and thermal radiation through said optical window.

31. The apparatus of claim 29, wherein said filament comprises a tungsten carbide filament.

32. The apparatus of claim 29, wherein said filament is located near said distal end.

33. The apparatus of claim 29, wherein said means for providing thermal radiation comprises a mirror fixedly and operatively located near said distal end, wherein said filament is located near said proximal end, wherein said shaft comprises a hollow waveguide, wherein thermal and optical radiation from said filament are transported through said hollow wave-guide and reflected off said mirror and through said optical window.

34. The apparatus of claim 33, further comprising a reflector operatively located near said filament to direct radiation emitted away from said distal end toward said mirror.

35. The apparatus of claim 22, wherein said shaft comprises an optical window, wherein said means for providing energy comprises means for providing electromagnetic radiation for transmission through said optical window to targeted tissue.

36. The apparatus of claim 35, wherein said means for delivering electromagnetic radiation comprises at least one optical fiber in said shaft.

37. The apparatus of claim 35, wherein said optical window is positioned such that light transmitted through said optical window deviates from said first plane and said second plane by an angle of at least 5 degrees.

38. The apparatus of claim 35, wherein said means for delivering electromagnetic radiation comprises a waveguide in the shaft.

39. The apparatus of claim 35, further comprising means for providing visible radiation for transmission through said optical window to aid in a determination of the location of said window when said window is beneath tissue.

40. The apparatus of claim 35, wherein said optical window comprises glass selected from a group consisting of quartz, fused silica and germanium.

41. The apparatus of claim 35, wherein said optical window comprises an optical filter.

42. The apparatus of claim 35, wherein said means for providing electromagnetic radiation include a source of laser light selected from the group consisting of a $CO_2$ laser, an erbium-YAG laser and a holmium laser.

43. The apparatus of claim 35, further comprising control means for controlling the delivery of electromagnetic radiation to said distal end of said shaft.

44. The apparatus of claim 35, wherein said shaft is hollow and has an inner surface selected from the group consisting of a reflective inner surface and a polished metal inner surface.

45. A method, comprising:

producing, with a first instrument, a substantially planar separation in human or animal tissue, creating two opposing tissue planes, wherein said first instrument comprises a shaft having a proximal end and a distal end and a plurality of protruding members fixedly attached on said distal end of said shaft, wherein said plurality of protruding members are positionally fixed relative to said shaft, wherein each protruding member of said plurality of protruding members is positionally fixed relative to any other protruding member, wherein said plurality of protruding members comprises a first protruding member and a second protruding member; and a lysing mechanism comprising a first electro-conductive lysing segment located between said first protruding member and said second protruding member, wherein said lysing segment is configured to cut on its distal side, wherein said plurality of protruding members is insulated from said lysing mechanism, wherein said plurality of protruding members define a first plane on one side of said lysing mechanism and further define a second plane on the side of said lysing mechanism that is opposite to that of said first plane, wherein said lysing mechanism is fixed in a location substantially parallel to and within the range extending from said first plane and said second plane, wherein said apparatus is configured to cut two opposing and substantially planar tissue planes that are parallel with said first plane and said second plane as said apparatus is pushed through tissue; and applying, with a second instrument, energy to at Least one tissue plane of said two opposing tissue planes.

* * * * *